(12) United States Patent
Shelton, IV et al.

(10) Patent No.: US 11,504,126 B2
(45) Date of Patent: Nov. 22, 2022

(54) CONTROL SYSTEM FOR CLIP APPLIER

(71) Applicant: Ethicon LLC, Guaynabo, PR (US)

(72) Inventors: Frederick E. Shelton, IV, Hillsboro, OH (US); Chester O. Baxter, III, Loveland, OH (US); Joshua Dean Young, Loveland, OH (US)

(73) Assignee: Cilag GmbH International, Zug (CH)

( * ) Notice: Subject to any disclaimer, the term of this patent is extended or adjusted under 35 U.S.C. 154(b) by 678 days.

(21) Appl. No.: 15/689,505

(22) Filed: Aug. 29, 2017

(65) Prior Publication Data

US 2019/0059897 A1 Feb. 28, 2019

(51) Int. Cl.
| | |
|---|---|
| *A61B 17/10* | (2006.01) |
| *A61B 17/128* | (2006.01) |
| *A61B 17/00* | (2006.01) |
| *A61B 90/00* | (2016.01) |
| *A61B 17/29* | (2006.01) |

(52) U.S. Cl.
CPC .......... *A61B 17/10* (2013.01); *A61B 17/1285* (2013.01); *A61B 17/105* (2013.01); *A61B 2017/00017* (2013.01); *A61B 2017/00309* (2013.01); *A61B 2017/00327* (2013.01); *A61B 2017/00398* (2013.01); *A61B 2017/2927* (2013.01); *A61B 2090/064* (2016.02); *A61B 2090/066* (2016.02)

(58) Field of Classification Search
CPC ................ A61B 17/10; A61B 17/1285; A61B 2090/064; A61B 2017/00309; A61B 2017/00327; A61B 2017/00017; A61B 2090/066; A61B 2017/2927; A61B 17/105; A61B 2017/00398
See application file for complete search history.

(56) References Cited

U.S. PATENT DOCUMENTS

| | | | |
|---|---|---|---|
| 5,322,055 A | 6/1994 | Davison et al. | |
| 5,558,671 A | 9/1996 | Yates | |
| 5,792,135 A | 8/1998 | Madhani et al. | |
| 5,817,084 A | 10/1998 | Jensen | |

(Continued)

FOREIGN PATENT DOCUMENTS

| | | |
|---|---|---|
| WO | 2014151621 A1 | 9/2014 |
| WO | 2014151952 A1 | 9/2014 |

OTHER PUBLICATIONS

U.S. Appl. No. 15/200,283 entitled "Methods, Systems, and Devices for Initializing a Surgical Tool" filed Jul. 1, 2016.

(Continued)

*Primary Examiner* — Todd J Scherbel
(74) *Attorney, Agent, or Firm* — Mintz Levin Cohn Ferris Glovsky and Popeo, P.C.

(57) ABSTRACT

Controls systems and methods are provided for controlling a surgical clip applier for applying surgical clips to a vessel, duct, shunt, etc., during a surgical procedure are provided. In an exemplary embodiment, a control system is provided for controlling at least one motor coupled to a drive system on a surgical clip applier device for driving one or more drive assemblies and thereby actuating one or more actuation assemblies. The control system can be configured to communicate with the drive system of the clip applier tool and to control and modify movement of one or more drive assemblies and actuation assemblies based on certain feedback.

11 Claims, 14 Drawing Sheets

(56) References Cited

U.S. PATENT DOCUMENTS

| | | |
|---|---|---|
| 5,873,873 A | 2/1999 | Smith et al. |
| 5,878,193 A | 3/1999 | Wang et al. |
| 5,980,510 A | 11/1999 | Tsonton et al. |
| 6,039,735 A | 3/2000 | Greep |
| 6,066,137 A | 5/2000 | Greep |
| 6,132,368 A | 10/2000 | Cooper |
| 6,168,605 B1 | 1/2001 | Measamer et al. |
| 6,231,565 B1 | 5/2001 | Tovey et al. |
| 6,325,811 B1 | 12/2001 | Messerly |
| 6,364,888 B1 | 4/2002 | Niemeyer et al. |
| 6,500,176 B1 | 12/2002 | Truckai et al. |
| 6,783,524 B2 | 8/2004 | Anderson et al. |
| 7,112,201 B2 | 9/2006 | Truckai et al. |
| 7,125,409 B2 | 10/2006 | Truckai et al. |
| 7,169,146 B2 | 1/2007 | Truckai et al. |
| 7,186,253 B2 | 3/2007 | Truckai et al. |
| 7,189,233 B2 | 3/2007 | Truckai et al. |
| 7,220,951 B2 | 5/2007 | Truckai et al. |
| 7,309,849 B2 | 12/2007 | Truckai et al. |
| 7,311,709 B2 | 12/2007 | Truckai et al. |
| 7,354,440 B2 | 4/2008 | Truckai et al. |
| 7,380,696 B2 | 6/2008 | Shelton, IV et al. |
| 7,381,209 B2 | 6/2008 | Truckai et al. |
| 7,404,508 B2 | 7/2008 | Smith et al. |
| 7,455,208 B2 | 11/2008 | Wales et al. |
| 7,506,790 B2 | 3/2009 | Shelton, IV |
| 7,524,320 B2 | 4/2009 | Tierney et al. |
| 7,549,564 B2 | 6/2009 | Boudreaux |
| 7,559,450 B2 | 7/2009 | Wales et al. |
| 7,654,431 B2 | 2/2010 | Hueil et al. |
| 7,691,098 B2 | 4/2010 | Wallace et al. |
| 7,780,054 B2 | 8/2010 | Wales |
| 7,784,662 B2 | 8/2010 | Wales et al. |
| 7,798,386 B2 | 9/2010 | Schall et al. |
| 7,806,891 B2 | 10/2010 | Nowlin et al. |
| 7,824,401 B2 | 11/2010 | Manzo et al. |
| 8,439,910 B2 | 5/2013 | Greep et al. |
| 8,461,744 B2 | 6/2013 | Wiener et al. |
| 8,469,252 B2 | 6/2013 | Holcomb et al. |
| 8,602,286 B2 | 12/2013 | Crainich et al. |
| 8,684,253 B2 | 4/2014 | Giordano et al. |
| 8,771,270 B2 | 7/2014 | Burbank |
| 8,986,302 B2 | 3/2015 | Aldridge et al. |
| 9,023,071 B2 | 5/2015 | Miller et al. |
| 9,072,536 B2 | 7/2015 | Shelton, IV et al. |
| 9,095,367 B2 | 8/2015 | Olson et al. |
| 9,119,657 B2 | 9/2015 | Shelton, IV et al. |
| 9,168,092 B2 | 10/2015 | Horner et al. |
| 9,393,037 B2 | 7/2016 | Olson et al. |
| 9,445,816 B2 | 9/2016 | Swayze et al. |
| 9,585,658 B2 | 3/2017 | Shelton, IV |
| 9,713,468 B2 | 7/2017 | Harris et al. |
| 9,713,471 B2 | 7/2017 | Holcomb et al. |
| 9,750,499 B2 | 9/2017 | Leimbach et al. |
| 2004/0097971 A1 | 5/2004 | Hughett |
| 2006/0079874 A1 | 4/2006 | Faller et al. |
| 2007/0191713 A1 | 8/2007 | Eichmann et al. |
| 2007/0282333 A1 | 12/2007 | Fortson et al. |
| 2008/0200940 A1 | 8/2008 | Eichmann et al. |
| 2009/0248038 A1 | 10/2009 | Blumenkranz et al. |
| 2010/0191282 A1 | 7/2010 | Harris et al. |
| 2010/0198248 A1 | 8/2010 | Vakharia |
| 2011/0015631 A1 | 1/2011 | Wiener et al. |
| 2011/0087218 A1 | 4/2011 | Boudreaux et al. |
| 2011/0087256 A1 | 4/2011 | Wiener et al. |
| 2012/0078139 A1 | 3/2012 | Aldridge et al. |
| 2012/0078243 A1 | 3/2012 | Worrell et al. |
| 2012/0078247 A1 | 3/2012 | Worrell et al. |
| 2012/0116379 A1 | 5/2012 | Yates et al. |
| 2012/0248167 A1* | 10/2012 | Flanagan ......... A61B 17/07207 227/2 |
| 2012/0292367 A1 | 11/2012 | Morgan et al. |
| 2012/0298719 A1* | 11/2012 | Shelton, IV ........... A61B 34/35 227/176.1 |
| 2013/0012957 A1 | 1/2013 | Shelton, IV et al. |
| 2013/0023868 A1 | 1/2013 | Worrell et al. |
| 2013/0030428 A1 | 1/2013 | Worrell et al. |
| 2013/0261648 A1 | 10/2013 | Laurent et al. |
| 2013/0325034 A1 | 12/2013 | Schena et al. |
| 2014/0005684 A1 | 1/2014 | Kim et al. |
| 2014/0005694 A1 | 1/2014 | Shelton, IV et al. |
| 2014/0005718 A1 | 1/2014 | Shelton, IV et al. |
| 2014/0151952 A1 | 6/2014 | Kozaki |
| 2014/0166728 A1 | 6/2014 | Swayze et al. |
| 2014/0171970 A1 | 6/2014 | Martin et al. |
| 2014/0263541 A1 | 9/2014 | Leimbach et al. |
| 2014/0276931 A1 | 9/2014 | Parihar et al. |
| 2014/0305995 A1 | 10/2014 | Shelton, IV et al. |
| 2015/0196298 A1 | 7/2015 | Menn et al. |
| 2015/0209059 A1 | 7/2015 | Trees et al. |
| 2015/0209573 A1 | 7/2015 | Hibner et al. |
| 2015/0272575 A1 | 10/2015 | Leimbach et al. |
| 2015/0282825 A1 | 10/2015 | Trees et al. |
| 2015/0365296 A1 | 12/2015 | Bunte et al. |
| 2016/0019918 A1 | 1/2016 | Juman |
| 2016/0019919 A1 | 1/2016 | Gale et al. |
| 2016/0089533 A1 | 3/2016 | Turner et al. |
| 2016/0175060 A1 | 6/2016 | Park |
| 2016/0287252 A1 | 10/2016 | Parihar |
| 2016/0367243 A1 | 12/2016 | Martin et al. |
| 2017/0056038 A1 | 3/2017 | Hess et al. |
| 2017/0172608 A1 | 6/2017 | Madan et al. |
| 2017/0196637 A1 | 7/2017 | Shelton, IV et al. |
| 2017/0202607 A1* | 7/2017 | Shelton, IV ............ H02J 7/342 |
| 2017/0202609 A1 | 7/2017 | Shelton, IV et al. |
| 2017/0296173 A1 | 10/2017 | Shelton, IV et al. |
| 2017/0296189 A1* | 10/2017 | Vendely ............... A61B 17/068 |
| 2017/0333033 A1 | 11/2017 | Valentine et al. |
| 2017/0340325 A1 | 11/2017 | Baril et al. |
| 2019/0059866 A1 | 2/2019 | Shelton, IV et al. |
| 2019/0059898 A1 | 2/2019 | Shelton, IV et al. |

OTHER PUBLICATIONS

U.S. Appl. No. 15/237,653 entitled "Methods, Systems, and Devices for Controlling a Motor of a Robotic Surgical System" filed Aug. 16, 2016.

U.S. Appl. No. 15/422,767 entitled "Robotic Surgical System and Methods for Articulation Calibration" filed Feb. 2, 2017.

U.S. Appl. No. 15/634,620 entitled "Surgical Stapler with Independently Actuated Drivers to Provide Varying Staple Heights" filed Jun. 27, 2017.

U.S. Appl. No. 15/674,075 entitled "Clip Retention for Surgical Clip Applier" filed Aug. 10, 2017.

U.S. Appl. No. 15/674,086 entitled "Surgical Clip Applier Jaw Alignment" filed Aug. 10, 2017.

U.S. Appl. No. 15/674,096 entitled "Surgical Device with Overload Mechanism" filed Aug. 10, 2017.

U.S. Appl. No. 15/674,121 entitled "Jaw for Clip Applier" filed Aug. 10, 2017.

U.S. Appl. No. 15/674,125 entitled "Clip Appliers with Extended Jaw Tip" filed Aug. 10, 2017.

U.S. Appl. No. 15/674,166 entitled "Surgical Clip Applier" filed Aug. 10, 2017.

U.S. Appl. No. 15/689,072 entitled "Methods, Systems, and Devices for Controlling Electrosurgical Tools" filed Aug. 29, 2017.

U.S. Appl. No. 29/613,511 entitled "Clip Applier Rotation Knob" filed Aug. 10, 2017.

U.S. Appl. No. 15/689,555, filed Aug. 29, 2017, Control System for Clip Applier.

U.S. Appl. No. 15/689,573, filed Aug. 29, 2017, Control System for Clip Applier.

* cited by examiner

CONTROL SYSTEM FOR CLIP APPLIER

FIELD

Control systems and methods are provided for controlling electrically-powered surgical clip appliers for applying clips to tissue, such as ducts, vessels, shunts, etc.

BACKGROUND

More and more surgical procedures are being performed using electrically-powered surgical devices that are either hand-held or coupled to a surgical robotic system. Such devices generally include one or more motors for driving various functions on the device, such as shaft rotation, articulation of an end effector, scissor or jaw opening and closing, firing or clips, staples, cutting elements, and/or energy, etc.

Some drawbacks of current electrically-powered surgical devices is the lack of control and tactile feedback that is inherent in a manually-operated device. Surgeons and other users accustomed to manually-operated devices often find that electrically-powered devices reduce their situational awareness because of the lack of feedback from the device. For example, electrically-powered devices do not provide users with any feedback regarding the progress of a clamping and/or sealing operation (e.g., an actuation button or switch is typically binary and provides no feedback on how much tissue has been cut, etc.) or the forces being encountered (e.g., toughness of the tissue, foreign objects). This lack of feedback can produce undesirable conditions. For example, if a motor's power is not adequate to perform the function being actuated, the motor can stall out. Without any feedback to a user, the user may maintain power during a stall, potentially resulting in damage to the device and/or the patient. Furthermore, even if the stall is discovered, users often cannot correct the stall by reversing the motor because a greater amount of force is available to actuate than may be available to reverse it (e.g., due to inertia when advancing). As a result, time-intensive extra operations can be required to disengage the device from the tissue. In addition, electrically-powered devices, such as powered surgical clip appliers, can be unable to accommodate changing loads experienced by the powered surgical clip applier.

Accordingly, there remains a need for improved devices and methods that address current issues with electrically-powered surgical devices.

SUMMARY

Control systems and methods for controlling a surgical clip applier are provided herein. In one embodiment, a surgical system is provided and includes a surgical clip applier having a shaft assembly with a shaft having a plurality of clips disposed therein and a pair of jaws at a distal end thereof. The clip applier shaft assembly can include a clip advancing assembly configured to feed a distal-most clip of the plurality of clips into the pair of jaws, and a clamping assembly configured to move the pair of jaws from an open position to a closed position to form the distal-most clip around tissue. The system can also include a drive assembly operably coupled to the clamping assembly and configured to drive the drive assembly through stages of clip formation in which a distal-most clip in the jaws is moved from an initial open configuration to a final closed configuration. A control system is provided for actuating the drive assembly. In one embodiment, the control system can have a stored predetermined threshold, and it can be configured to stop movement of the drive assembly during the stages of clip formation if the stored predetermined threshold is exceeded.

The system can vary in a number of ways. For example, the drive assembly can be operably coupled to at least one motor and the at least one stored predetermined threshold can include at least one motor load threshold based on a load of the motor. As another example, the at least one stored predetermined threshold can include a velocity threshold based on a velocity of the clamping assembly.

As yet another example, the stages of clip formation can include a first stage in which the clip is moved from the initial open configuration to a partially closed configuration, and a second stage in which the clip is moved from the partially closed configuration to the final closed configuration. The at least one stored predetermined threshold can include a first threshold and a second threshold that differs from the first threshold. The control system can be configured to stop movement of the drive assembly during the first stage of clip formation if the first threshold is exceeded, and the control system can be further configured to stop movement of the drive assembly during the second stage of clip formation if the second threshold is exceeded. Furthermore, the second threshold can be greater than the first threshold.

In other implementations, the drive assembly can be disposed within a housing coupled to a proximal end of the clip applier shaft assembly. In other implementations, the drive assembly can include a first housing on a robotic arm having the at least one motor disposed therein, and a second housing on a proximal end of the clip applier shaft assembly and having at least one connector for coupling to the at least one motor in the first housing.

In another embodiment, a surgical clip applier system is provided that includes an electromechanical tool shaft assembly. The electromechanical tool shaft assembly can include an instrument shaft, an end effector at a distal end thereof having a pair of jaws movable between open and closed positions, a clip stack disposed within the instrument shaft and including a plurality of clips, a clip advancing assembly extending through the instrument shaft and configured to feed a distal-most clip of the clip stack into the pair of jaws, and a clamping assembly configured to move the pair of jaws from the open position to the closed position to move the distal-most clip in the pair of jaws from the open configuration to a tissue-engaging configuration. The surgical clip applier system can also include a drive system operably coupled to the electromechanical tool shaft assembly. The drive system can include at least one motor configured to drive the clamping assembly. The drive system can be configured to drive the clamping assembly through stages of clip formation including a first stage in which the jaws can be moved from the open configuration to a partially closed configuration to partially close a distal-most clip disposed within the jaws, and a second stage in which the jaws are moved from the partially closed configuration to the closed configuration to move the clip to the tissue-engaging configuration. The surgical clip applier system can further include a control system configured to actuate the drive system and thereby control movement of the clamping assembly. The control system can have a first threshold for the first stage of clip formation and a second threshold for the second stage of clip formation. The control system can be configured to terminate movement of the clamping assembly during the first stage if the first threshold is exceeded, and the control system being configured to terminate movement of the clamping assembly during the second stage if the second threshold is exceeded.

The surgical system can vary in a number of ways. For example, the second threshold can be greater than the first threshold. As another example, the first and second threshold can include motor load thresholds that limit a load on the at least one motor. As yet another example, the drive system can be disposed within a housing coupled to a proximal end of the instrument shaft. In some implementations the drive system can include a first housing on a robotic arm having the at least one motor disposed therein, and a second housing on a proximal end of the instrument shaft, the second housing having at least one connector for coupling to the at least one motor in the first housing.

In another aspect, a method for applying a clip to tissue is provided. The method can include manipulating a clip applier device to position tissue within a clip seated in a pair of jaws on a distal end of a elongate shaft of the clip applier device, and actuating a drive system to cause a clamping assembly to move the pair of jaws from an open configuration to a closed configuration to cause the clip to engage the tissue. A control system operably coupled to the drive system can stop movement of the drive system and thus the clamping assembly if a first predetermined threshold is exceeded during actuation of the drive system.

The method can vary in a number of ways. For example, the control system can stop movement of the drive system and thus the clamping assembly if a second predetermined threshold is exceeded during actuation of the drive system. The control system can apply the first threshold for a first stage of clip formation and the second threshold for a second stage of clip formation. Furthermore, the first stage of clip formation can include moving the jaws from the open configuration to a partially closed configuration thereby partially closing the clip disposed within the jaws. The second stage of clip formation can include moving the jaws from the partially closed configuration to the closed configuration to move the clip to a tissue-engaging configuration. In some implementations, the second predetermined threshold can be greater than the first predetermined threshold and the first predetermined threshold.

As another example, the control system can wirelessly communicate with the drive system to actuate the drive system. As yet another example, manipulating a clip applier device can include manipulating a user input device wirelessly coupled to a surgical robotic system having the clip applier coupled thereto. In some implementations, manipulating a surgical clip applier device includes manipulating a handle housing of the clip applier device.

In another embodiment, a surgical clip applier system is provided. The surgical clip applier system can include a clip applier shaft assembly having a pair of jaws at a distal end thereof, and having a shaft with a plurality of clips disposed therein. The clip applier shaft assembly can include a clip feed assembly configured to feed a distal-most clip of the plurality of clips into the pair of jaws, and a clamping assembly configured to move the pair of jaws from an open position to a closed position to form the distal-most clip around tissue. The surgical clip applier system can also include a drive assembly operably coupled to the clamping assembly and to a motor for driving the clamping assembly through a first stage of clip formation in which a clip in the jaws is moved from an initial open configuration to a partially closed configuration, and to further drive the clamping assembly through a second stage of clip formation in which the clip is moved from the partially closed configuration to a final closed configuration. The clip applier system can further include a control system configured to control the motor so as to control a velocity of the clamping assembly during the first stage of clip formation, and to terminate actuation of the motor and thus the drive assembly during the second stage of clip formation if a load on the motor exceeds a first predetermined load threshold.

The clip applier system can vary in a number of ways. For example, the control system can be configured to terminate actuation of the motor and thus the drive assembly during the first stage of clip formation if a load on the motor exceeds a second predetermined load threshold. As another example the first predetermined threshold can be greater than the second predetermined threshold.

As yet another example, the control system can be configured to monitor a displacement of the clamping assembly and, based on a predefined displacement, reduce the velocity of the clamping assembly. In some embodiments, a distal end of each of the jaws of the pair of jaws can come into contact with each other at the predefined displacement.

In some implementations, the drive assembly can be disposed within a housing coupled to a proximal end of the clip applier shaft assembly. In other implementations, the drive assembly can include a first housing on a robotic arm having the motor disposed therein, and a second housing on a proximal end of the clip applier shaft assembly and having at least one connector for coupling to the motor in the first housing.

In another embodiment, a surgical clip applier system is provided that includes an electromechanical tool shaft assembly. The electromechanical tool shaft assembly can include an instrument shaft, an end effector at a distal end thereof having a pair of jaws movable between open and closed positions, a clip stack disposed within the instrument shaft and including a plurality of clips, a clip advancing assembly extending through the instrument shaft and configured to feed a distal-most clip of the clip stack into the pair of jaws, and a clamping assembly configured to move the pair of jaws from the open position to the closed position to move the distal-most clip in the pair of jaws from the open configuration to a tissue-engaging configuration. The surgical clip applier system can also include a drive system operably coupled to the electromechanical tool shaft assembly and having a motor configured to drive the clamping assembly. The drive assembly can drive the clamping assembly through a first stage in which the jaws are moved from the open configuration to a partially closed configuration to thereby partially close a distal-most clip disposed within the jaws, and a second stage in which the jaws are moved from the partially closed configuration to the closed configuration to thereby move the clip to the tissue-engaging configuration. The clip applier system can further include a control system configured to actuate the drive system and thereby control movement of the clamping assembly so as to control a velocity of the clamping assembly during the first stage, and to terminate actuation of the motor and thus the drive assembly during the second stage if a load on the motor exceeds a first predetermined load threshold.

The surgical clip applier system can vary in a number of ways. For example, the control system can be configured to terminate actuation of the motor and thus the drive assembly during the first stage of clip formation if a load on the motor exceeds a second predetermined load threshold. In some embodiments, the first predetermined threshold can be greater than the second predetermined threshold.

As another example, the control system can be configured to monitor a displacement of the clamping assembly and, based on a predefined displacement, lower the velocity of the clamping assembly. In some embodiments, a distal end of each of the jaws of the pair of jaws come into contact with each other at the predefined displacement.

In some implementations, the drive assembly can be disposed within a housing coupled to a proximal end of the instrument shaft. In other implementations, the drive system can include a first housing on a robotic arm having the motor disposed therein, and a second housing on a proximal end of the instrument shaft and having a connector for coupling to the motor in the first housing.

In another aspect, a method for applying a clip to tissue is provided. The method can include manipulating a clip applier device to position tissue within a clip seated in a pair of jaws on a distal end of a elongate shaft of the clip applier device, and actuating a drive system to cause a motor to drive a clamping assembly to thereby move the pair of jaws through a first stage of formation in which the clip is moved from an open configuration to partially closed configuration, and to further move the pair of jaws through a second stage of formation in which the clip is moved from the partially closed configuration to a closed configuration to cause the clip to engage the tissue. A control system coupled to the drive system can actuate the drive system to control movement of the clamping assembly at a velocity during the first stage of formation, and the control system can stop movement of the drive system and thus the clamping assembly during the second stage of formation if a load on the motor exceeds a first predetermined threshold load.

The method can vary in a number of ways. For example, the control system can stop movement of the drive system and thus the clamping assembly during the first stage of formation if a load on the motor exceeds a second predetermined threshold load. In some embodiments, the first predetermined threshold can be greater than the second predetermined threshold. As another example, the control system can wirelessly communicate with the drive system to actuate the drive system.

In some implementations, manipulating the clip applier device can include manipulating a user input device wirelessly coupled to a surgical robotic system having the clip applier coupled thereto. In other implementations, manipulating the surgical clip applier device can include manipulating a handle housing of the clip applier device.

In certain embodiments, a surgical clip applier system is provided and includes a clip applier shaft assembly having a shaft with a plurality of clips disposed therein and a pair of jaws at a distal end thereof. The clip applier shaft assembly can include a clip advancing assembly configured to feed a distal-most clip of the plurality of clips into the pair of jaws, and a clamping assembly configured to move the pair of jaws from an open position to a closed position to move the distal-most clip around tissue from an open configuration to a closed tissue-engaging configuration. The system can also include a drive assembly operably coupled to the clamping assembly and to a motor configured to drive the clamping assembly to move the jaws between an open position and a closed position. The system can further include a control system configured to control the motor, and configured to actuate a clip stability test after the pair of jaws is moved to the closed position. The clip stability test can be configured to cause the pair of jaws to move from the closed position to a partially open configuration and back to the closed position.

In one embodiment, the control system can be configured to monitor a force required by the drive assembly to move the clamping assembly during the clip stability test. The control system can be configured to indicate whether the distal-most clip in the jaws is engaged with tissue by comparing the force monitored during the clip stability test to a threshold force. The predetermined threshold force can be, for example, a maximum force required to move the clamping assembly to cause the jaws to move to the closed position. The control system can be configured to determine the maximum force when the clamping assembly is driven to move the jaws from the open position to the closed position, prior to the control system actuating the clip stability test. In certain embodiments, the control system can be configured to determine that the distal-most clip is properly engaged in tissue if the monitored force exceeds the a threshold force prior to completion of the clip stability test, and the control system can configured to determine that the distal-most clip is not properly engaged in tissue if the monitored force does not exceed a threshold force prior to completion of the clip stability test.

In other aspects, the clip stability test can further be configured to cause the pair of jaws to rotate in at least one direction about a longitudinal axis of the clip applier shaft assembly after causing the drive assembly to move the jaws to the partially open configuration and before causing the drive assembly to move the jaws back to closed position.

In another embodiment, a surgical clip applier system is provided and includes an electromechanical tool shaft assembly having an instrument shaft, an end effector at a distal end thereof having a pair of jaws movable between open and closed positions, a clip stack disposed within the instrument shaft and comprising a plurality of clips, a clip advancing assembly extending through the instrument shaft and configured to feed a distal-most clip of the clip stack into the pair of jaws, and a clamping assembly configured to move the pair of jaws from the open position to the closed position to move the distal-most clip in the pair of jaws from the open configuration to a closed tissue-engaging configuration. The system can also include a drive system operably coupled to the electromechanical tool shaft assembly and having a motor configured to drive the clamping assembly to thereby move the jaws from the open configuration to the tissue-engaging configuration. The system can also include a control system operably coupled to the motor and configured to actuate a clip stability test after the pair of jaws is moved to the closed position. The clip stability test can be configured to cause the drive system to move the jaws from the closed position to a partially open configuration and back to the closed position. The control system can be configured to monitor a force required by the drive system to move the jaws during the clip stability test to determine whether a clip in the tissue-engaging configuration is properly engaged in tissue.

In one aspect, the control system can include a force threshold having a force value equivalent to a measured closing force. The measured closing force can be a force required to advance the clamping assembly to move the jaws to the closed position, and the measured closing force can be determined by the control system prior to actuation of the clip stability test when the jaws are in the closed position. The control system can be configured to determine that the clip in the closed tissue-engaging configuration is properly engaged in tissue if a test force measured by the control system during actuation of the clip stability test exceeds the force threshold before the clamping assembly moves the jaws back to the closed position. The control system can be configured to determine that the clip in the closed tissue-engaging configuration is not properly engaged in tissue if a test force measured by the control system during actuation of the clip stability test does not exceed the force threshold before the clamping assembly moves the jaws back to the closed position.

In other embodiments, the clip stability test can further be configured to cause the pair of jaws to rotate in at least one direction about a longitudinal axis of the clip applier shaft assembly after causing the drive assembly to move the jaws to the partially open configuration and before causing the drive assembly to move the jaws back to closed position. In certain aspects, the drive system can be disposed within a housing coupled to a proximal end of the instrument shaft. In other aspects, the drive system can be a first housing on a robotic arm having the motor disposed therein, and a second housing on a proximal end of the instrument shaft and having a connector for coupling to the motor in the first housing.

Methods for applying a clip to tissue are also provided and in one embodiment can include manipulating a clip applier device to position tissue within a clip seated in a pair of jaws on a distal end of an elongate shaft of the clip applier device, and actuating a drive system to cause a motor to drive a clamping assembly to thereby move the pair of jaws to a closed configuration thereby causing a clip to form a closed tissue-engaging configuration. A control system coupled to the drive system can subsequently actuate a clip stability test that causes the drive system to move the pair of jaws from the closed position to a partially open configuration and back to the closed position. The control system can monitor a force required by the drive system to move the pair of jaws during the clip stability test to determine if a clip in the closed tissue-engaging configuration is properly engaged with tissue.

In one embodiment, the control system can include a force threshold having a force value equivalent to a measured closing force. The measured closing force can be determined by the control system prior to actuation of the clip stability test when the jaws are in the closed position.

The control system can determine that the clip in the closed tissue-engaging configuration is properly engaged in tissue if a test force measured by the control system during actuation of the clip stability test exceeds the force threshold before the clamping assembly moves the jaws back to the closed position. The control system can determine that the clip in the closed tissue-engaging configuration is not properly engaged in tissue if a test force measured by the control system during actuation of the clip stability test does not exceed the force threshold before the clamping assembly moves the jaws back to the closed position. In other embodiments, the control system can wirelessly communicate with the drive system to actuate the drive system.

DETAILED DESCRIPTION

Figure 1:
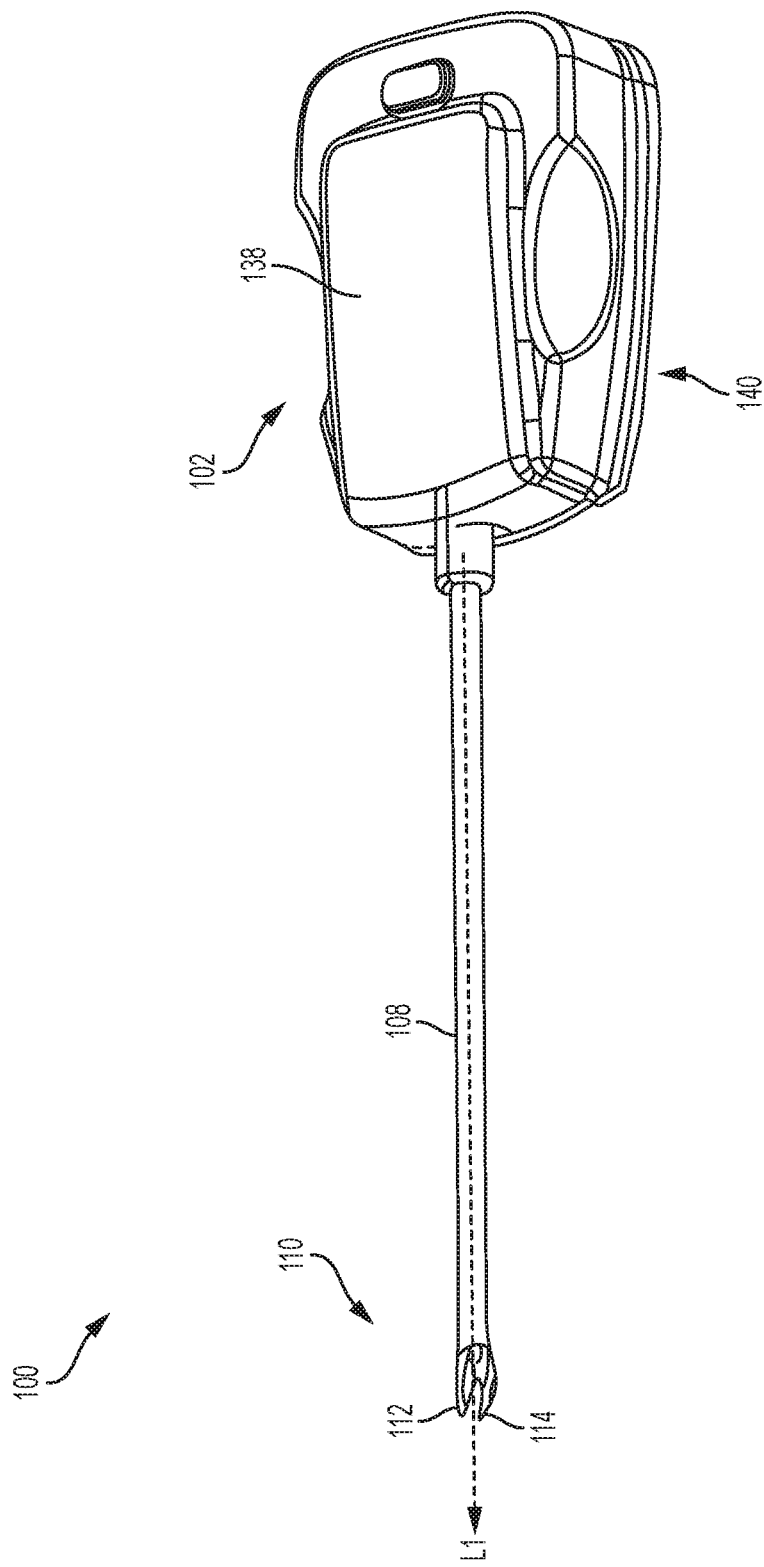
FIG. 1 is a perspective view of one embodiment of a surgical clip applier for use with a robotic system.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices, systems, and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

It will be appreciated that the terms "proximal" and "distal" are used herein with reference to a user, such as a clinician, gripping a handle of an instrument. Other spatial terms such as "front" and "rear" similarly correspond respectively to distal and proximal. It will be further appreciated that for convenience and clarity, spatial terms such as "vertical" and "horizontal" are used herein with respect to the drawings. However, surgical instruments are used in many orientations and positions, and these spatial terms are not intended to be limiting and absolute.

Systems and methods are provided for controlling a surgical clip applier for applying a clip to tissue, such as ducts, vessels, shunts, etc., during a surgical procedure. The surgical clip applier systems can be configured for use with a surgical clip applier having a housing and an elongate shaft assembly extending therefrom with a jaw assembly coupled to a distal end of the elongate shaft assembly. The jaw assembly can include first and second jaws that are configured to receive and form a clip therebetween. The first and second jaws can be movable between an open position and a closed position. In certain embodiments, the jaw assembly can articulate relative to a proximal part of the elongate shaft about an articulation section along the elongate shaft. The elongate shaft assembly can include various actuation assemblies for actuating the surgical clip applier. For example, the surgical clip applier can include a clip advancing assembly configured to allow a clip to be delivered between the jaws, a clip forming assembly configured to close the jaws to form the clip therebetween, a rotation assembly configured to rotate the elongate shaft assembly and jaw assembly, and/or an articulation assembly configured to allow the jaw assembly to be selectively articulated about an articulation section along the elongate shaft. The clip applier can further include a drive system operably coupled between at least one motor and at least one of the actuation assemblies. The drive system can include one or more drive assemblies configured to control the various actuation assemblies. The surgical clip applier system can also include a control system operably coupled to the at least one motor and configured to actuate the at least one motor to drive the drive system. In certain embodiments, the control system can be configured to modify a force being applied to the drive system by the at least one motor based at least in part on one or more predetermined thresholds, such as a motor force threshold, and/or a position of one or more actuation assemblies. The control system can allow for powered actuation of the drive system, as opposed to manual actuation via a trigger, and it can enable controlled movement of the actuation assemblies, such as the clip advancing assembly, clip forming assembly, rotation assembly, and articulation assembly.

An exemplary surgical clip applier system can include a variety of features to facilitate application of a surgical clip, as described herein and illustrated in the drawings. However, a person skilled in the art will appreciate that the surgical clip applier systems can include only some of these features and/or it can include a variety of other features known in the art. The surgical clip applier systems described herein are merely intended to represent certain exemplary embodiments. Moreover, while the drive and control systems are described in connection with surgical clip appliers, these systems can be used in connection with any type of surgical device. Further, a person skilled in the art will appreciate that the surgical clip applier systems described herein have application in conventional minimally-invasive and open surgical instrumentation as well application in robotic-assisted surgery.

Surgical Clip Applier

Figure 2:
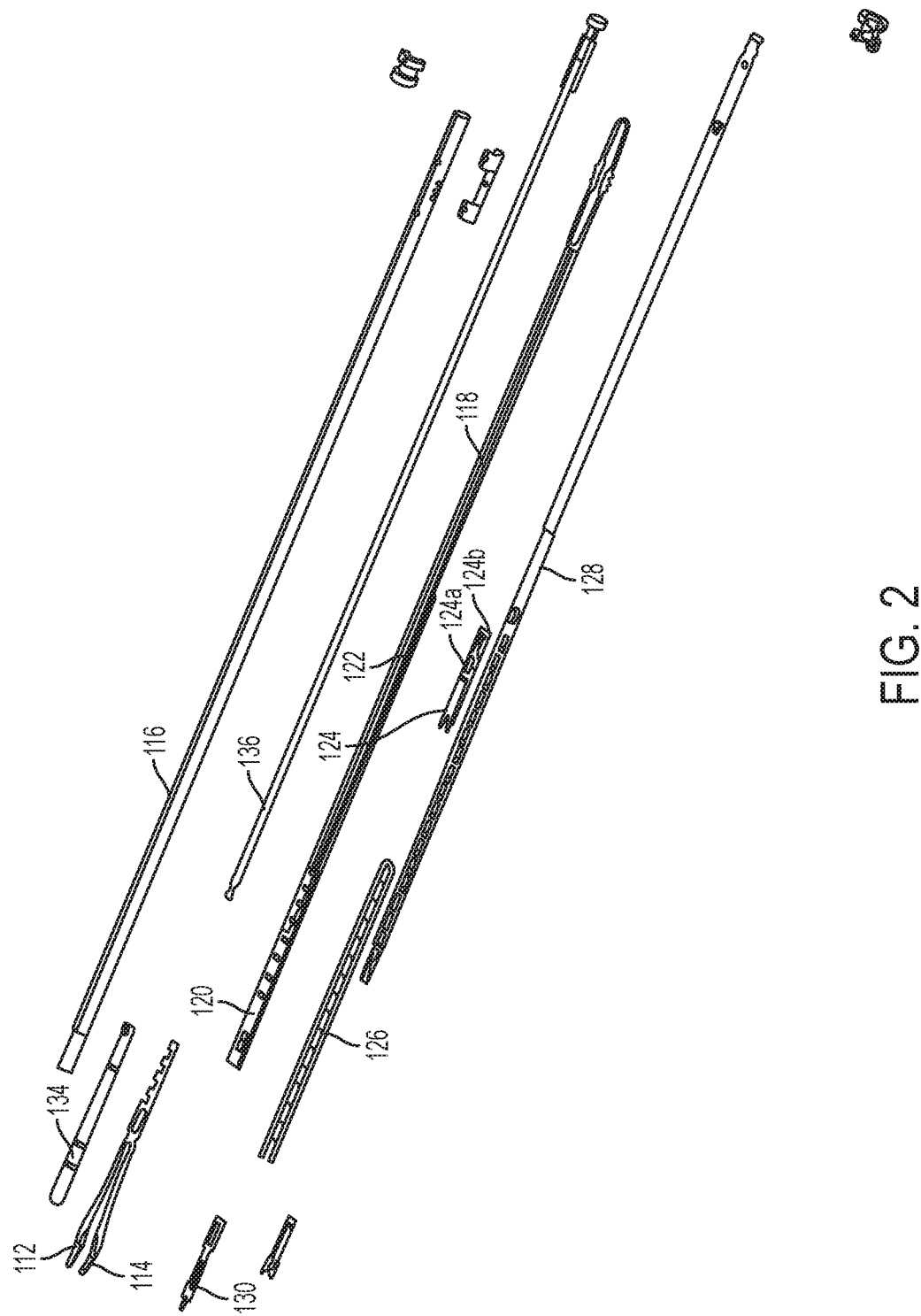
FIG. 2 is an exploded view of a shaft assembly of the surgical clip applier of FIG. 1.

As indicated above, in an exemplary embodiment control systems are provided for controlling actuation of a surgical clip applier device. FIGS. 1-2 illustrate one embodiment of a surgical clip applier 100 for use with a robotics system including a control system. Additional details regarding surgical clip appliers, such as the surgical clip applier described herein, are disclosed in U.S. Patent Publication No. 2016/0287252 A1, which is herein incorporated by reference. Other exemplary surgical clip appliers are disclosed in U.S. application Ser. No. 15/674,166, filed on Aug. 10, 2017, and entitled "Surgical Clip Applier," U.S. application Ser. No. 15/674,125, filed on Aug. 10, 2017, and entitled "Clip Appliers with Extended Jaw Tip," U.S. application Ser. No. 15/674,075, filed on Aug. 10, 2017, and entitled "Clip Retention for Surgical Clip Applier," U.S. application Ser. No. 15/674,086, filed on Aug. 10, 2017, and entitled "Surgical Clip Applier Jaw Alignment," U.S. application Ser. No. 15/674,096, filed on Aug. 10, 2017, and entitled "Surgical Device with Overload Mechanism," U.S. application Ser. No. 15/674,121, and entitled "Jaw for Clip Applier," and U.S. application Ser. No. 29/613,511, filed on Aug. 10, 2017, and entitled "Clip Applier Rotation Knob," each of which is hereby incorporated by reference herein in its entirety.

The illustrated surgical clip applier 100 is configured to be used with a robotic system that is operable by inputs from an operator (i.e., a surgeon), however the surgical clip applier can be configured as a hand-held device. The illustrated surgical clip applier 100 includes a tool mounting portion 102 that is configured to couple to a robotic system. An elongate shaft assembly 108 extends distally from the tool mounting portion 102 and a jaw assembly 110 is coupled to a distal end of the elongate shaft assembly 108. The elongate shaft assembly 108 can include one or more actuation assemblies. The actuation assemblies can include a clip advancing assembly, a clip forming assembly, a rotation assembly, and an articulation assembly, which are discussed in more detail below. The jaw assembly can include first and second jaws 112, 114 that are movable between open and closed positions. The first and second jaws 112, 114 include opposed inward facing surfaces and each inward facing surface has a clip track formed therealong for receiving and guiding legs of a clip into the first and second jaws 112, 114. When the first and second jaws 112, 114 are in the open position with a clip positioned therebetween, tissue can be positioned between the legs of the clip. With the tissue positioned between the legs of the clip, the first and second jaws 112, 114 can be moved to the closed position to thereby form and secure the clip to the tissue. After the clip has been formed, the first and second jaws 112, 114 can be reopened to allow the formed clip to be released from the jaws and remain secured to the tissue.

The tool mounting portion 102 of the surgical clip applier 100 can include a drive system 150 having one or more drive assemblies configured to control the various actuation assemblies, which will be discussed in more detail below with respect to FIG. 3. The drive system can be contained within a housing 138 having an interface 140 for mechanically and electrically coupling the tool mounting portion 102 of the surgical clip applier 100 to one or more motors of the robotics system.

Rotation Assembly and Shaft Rotation Drive Assembly

In some embodiments, the surgical clip applier 100 can include a rotation assembly that allows the elongate shaft assembly 108 and/or the jaw assembly 110 to be rotated with respect to the tool mounting portion 102 and about the longitudinal axis L1. The rotation assembly can be operably coupled to a rotation drive assembly 152 of the drive system 150. The rotation drive assembly 152 can translate force from a motor to the rotation assembly to rotate the elongate shaft assembly 108 and/or the jaw assembly 110. While the rotation drive assembly 152 can have a variety of configurations, in some embodiments, as shown in FIG. 3, the rotation drive assembly 152 can include a first spiral worm gear 158 in meshing engagement with a second spiral worm gear 160 that is mechanically coupled to a proximal portion of the elongate shaft assembly 108. When the rotation drive assembly 152 is activated, the first spiral worm gear 158 drives the second spiral worm gear 160, thereby causing rotation of the elongate shaft assembly 108 and the jaw assembly 110 about the longitudinal axis L1. It will be appreciated that a direction of rotation of the first spiral worm gear 158 determines the direction of rotation of the elongate shaft assembly 108 and/or the jaw assembly 110 about the longitudinal axis L1. For example, when the first spiral worm gear 158 rotates in a first direction, the elongate shaft assembly 108 and/or the jaw assembly 110 will rotate in a corresponding direction. When the first spiral worm gear 158 rotates in a second direction, opposite the first direction, the elongate shaft assembly 108 and/or the jaw assembly 110 will rotate in a direction opposite the direction of rotation caused by rotation of the first spiral worm gear 158 in the first direction.

Clip Advancing Assembly and Clip Advancing Drive Assembly

As indicated above, the surgical clip applier 100 can also include a clip advancing assembly for advancing a clip into the jaws. As shown in FIG. 2, the elongate shaft assembly 108 includes an outer tube 116 that houses a jaw retainer shaft 118 including a clip track 120. The elongate shaft assembly 108 further includes a feeder shoe 124 slidably disposed along the clip track 120 and including first and second tangs 124a, 124b that can advance a series of clips 126 positioned within the clip track 120. The elongate shaft assembly 108 further includes a feed bar 128 that drives the feeder shoe 124 distally through the clip track 120 to advance the series of clips 126 toward the jaw assembly 110. The feed bar 128 can include an advancer assembly 130 configured to advance a distal-most clip into the jaws 112, 114 when the feed bar 128 is distally advanced. Distal advancement of the feed bar 128 can also assist in advancing the series of clips 126 along the clip track 120. For example, the feed bar 128 can be moved distally to allow a detent in the feed bar 128 to engage the second tang 124b of the feeder shoe 124 thereby moving the feeder shoe 124 distally within the clip track 120. As the feed bar 128 is moved distally, the first tang 124a can engage an opening in the clip track 120, thereby advancing the series of clips 126 towards the jaw assembly 110. The feed bar 128 can then be moved proximally thereby allowing the second tang 124b of the feeder shoe 124 to slide into a more proximal detent formed in the feed bar 128 and allow the series of clips 126 to advance further distally when the feed bar 128 is caused to move distally again.

Figure 3:
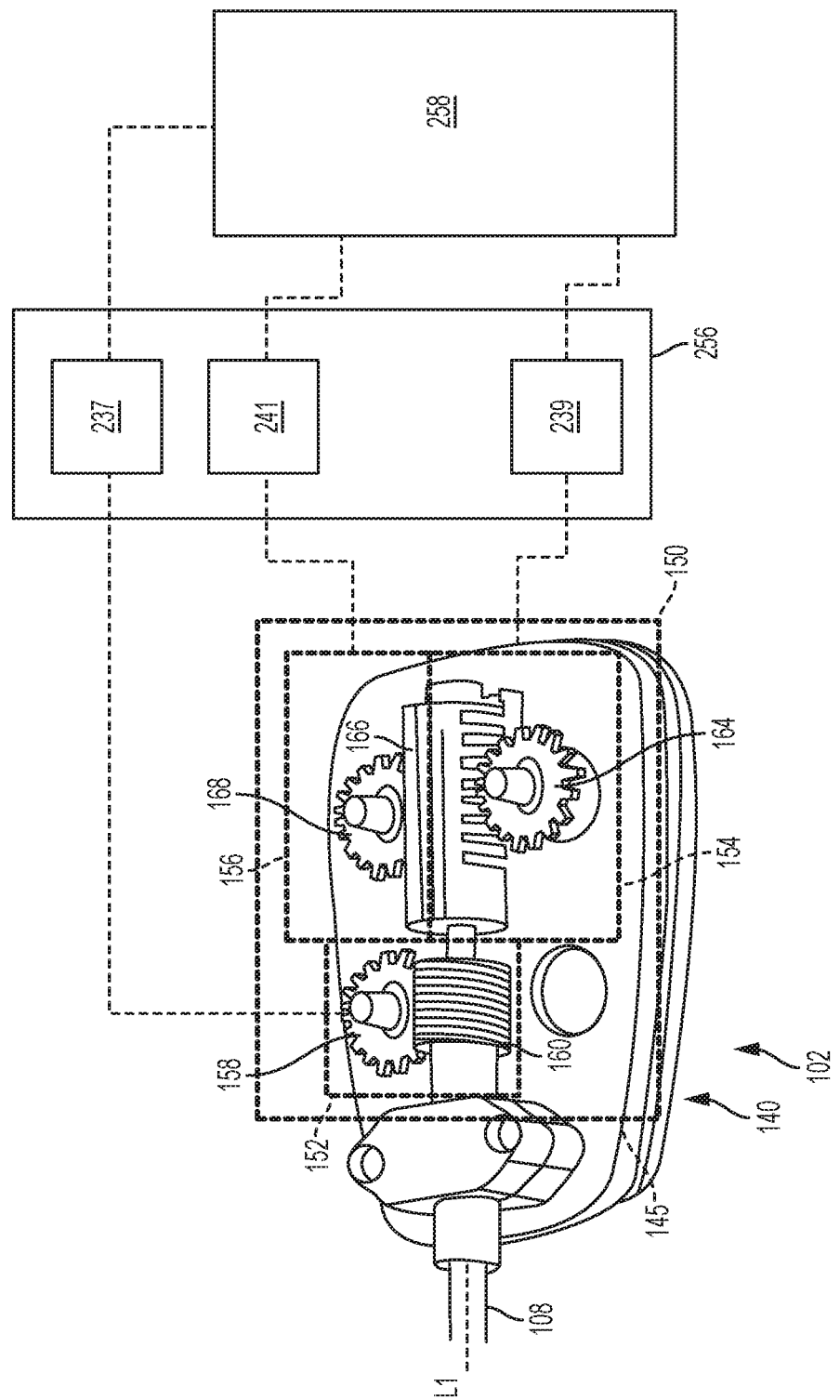
FIG. 3 is a perspective, partially schematic view of the surgical clip applier of FIG. 1 with a portion of the housing removed and showing a drive system of the surgical tool being coupled to motors that are operably coupled to a control system.

The aforementioned components of the clip advancing assembly can be operably coupled to a clip advancing drive assembly 154 of the drive system 150, shown in FIG. 3. The clip advancing drive assembly 154 can translate force from a motor to the clip advancing assembly to advance a distal-most clip into the jaw assembly 110. While the clip advancing drive assembly 154 can have a variety of configurations, in some embodiments, as shown in FIG. 3, the clip advancing drive assembly 154 can include a feed gear 164 in meshing engagement with a rack gear 166 that is coupled to the feed bar 128. When the clip advancing drive assembly 154 is activated, the feed gear 164 drives the rack gear 166 and feed bar 128 longitudinally along the axis L1. Application of a rotary motion of the feed gear 164 in a first direction can result in distal motion of the feed bar 128 to thereby load a distal-most clip into the jaw assembly 110, and application of rotary motion in a direction opposite the first direction can result in proximal motion of the feed bar 128.

Clip Forming Assembly and Clip Forming Drive Assembly

The elongate shaft assembly 108 of the surgical clip applier can also include a clip forming assembly that operates to close the jaws 112, 114 and form a clip positioned therebetween. As shown in FIG. 2, the clip forming assembly can include a cam 134 that can slidably mate to the jaw assembly 110. The clip forming assembly can also include a push rod 136 slidably disposed within the push rod channel 122 and coupled to the cam 134 to move the cam 134 relative to the jaw assembly 110. In operation, the push rod 136 can be driven distally, thereby driving the cam 134 over the jaws 112, 114, which closes the jaws and forms the clip positioned therebetween. The cam 134 can then be retracted, thereby leaving the formed clip within the tissue.

The clip forming assembly can be operably coupled to a clip forming drive assembly 156 of the drive system 150, shown in FIG. 3. The clip forming drive assembly 156 can translate force from a motor to the clip forming assembly to form a clip positioned between the jaws 112, 114. While the clip forming drive assembly 156 can have a variety of configurations, in some embodiments, as shown in FIG. 3, the clip forming drive assembly 156 can include a forming gear 168 in meshing engagement with the rack gear 166 that is coupled to the push rod 136. When the clip forming drive assembly 156 is activated, the forming gear 168 rotates, which drives the rack gear 166 longitudinally along the axis L1, thereby driving the push rod 136 and cam 154. Distal motion of the cam 154 can cause the jaws 112, 114 of the jaw assembly 110 to close, thereby forming a clip positioned between the jaws 112, 114. Proximal motion of the cam 154 can cause the jaws 112, 114 of the jaw assembly 110 to open, thereby releasing the clip formed in tissue, as described above. It will be appreciated that application of a rotary motion of the forming gear 168 in a first direction will result in distal motion of the cam 154, and application of rotary motion in a direction opposite the first direction will result in proximal motion of the cam 154.

Articulation Assembly and Articulation Drive Assembly

Figure 4:
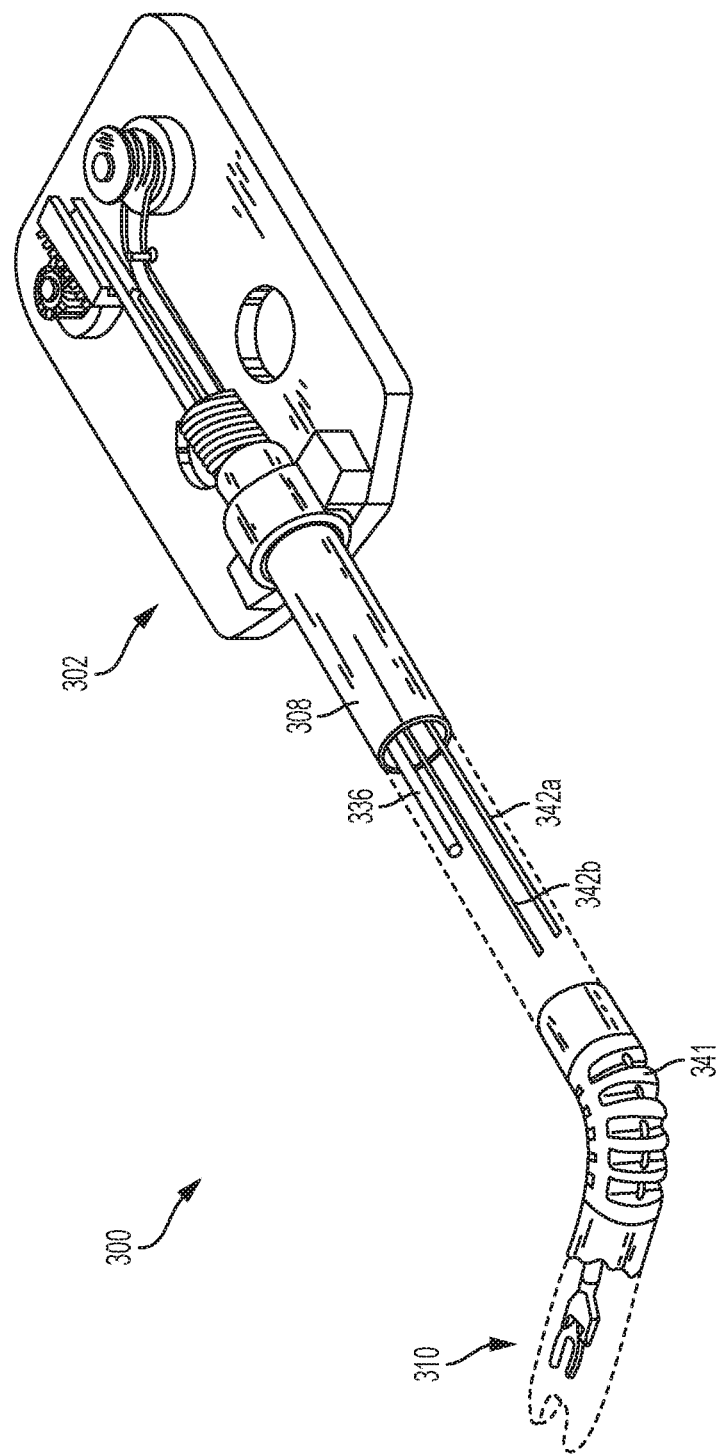
FIG. 4 is a perspective view of another embodiment of a surgical clip applier for use with a robotic system.

FIG. 4 shows another embodiment of a surgical clip applier 300 that can be coupled to a surgical robotic system and that includes an articulation assembly that allows a jaw assembly 310 of the clip applier 300 to be articulated. As shown in FIG. 4, the surgical clip applier 300 includes a tool mounting portion 302 having an elongate shaft assembly 308 extending distally therefrom. The elongate shaft assembly 308 includes a jaw assembly 310 coupled to a distal end thereof. The surgical clip applier 300 can generally be similar to the surgical clip applier 100 described above with regard to FIGS. 1-2, but with the addition of the articulation assembly. Accordingly, the surgical clip applier 300 can also include a rotation assembly, clip advancing assembly, and clip forming assembly, as described above with regard to the surgical clip applier 100 shown in FIGS. 1-2.

In order to allow for articulation, the elongate shaft assembly 308 can have a flexible articulation section 341. The articulation assembly can also include first and second articulation cables 342a, 342b that extend from the tool mounting portion 302, down the length of the elongate shaft assembly 308, and that are anchored on opposite sides of the elongate shaft assembly 308 at a position distal of the articulation section 341. Accordingly, by shortening the length of one of the articulation cables 342a, 342b, the jaw assembly 310 can be articulated about the articulation section 341 in that direction. For example, if the second articulation cable 342b is shortened relative to the first articulation cable 342a, the jaw assembly 310 will be articulated in a direction corresponding to the second articulation cable 342b, as shown in FIG. 4.

In order to accommodate articulation of the jaw assembly 310, the elongate shaft assembly 308 can include various flexible components extending therethrough. For example the elongate shaft assembly 308 can include a flexible push rod 336 that can accommodate articulation while maintaining sufficient rigidity to advance the cam 154 for closing first and second jaws of the jaw assembly 310 and forming clips positioned between the jaws. Additionally, other components such as those described above with regard to the elongate shaft assembly 108 shown in FIGS. 1-2 can be flexible. In some embodiments, certain components of the elongate shaft assembly 308 can be positioned distally of the flexible neck, adjacent to, or within, the jaw assembly 310. For example, the elongate shaft assembly 308 can include a shortened clip track positioned adjacent to the jaw assembly 310. Such a configuration would facilitate use of rigid components without compromising the ability to articulate the jaw assembly 310.

Figure 5:
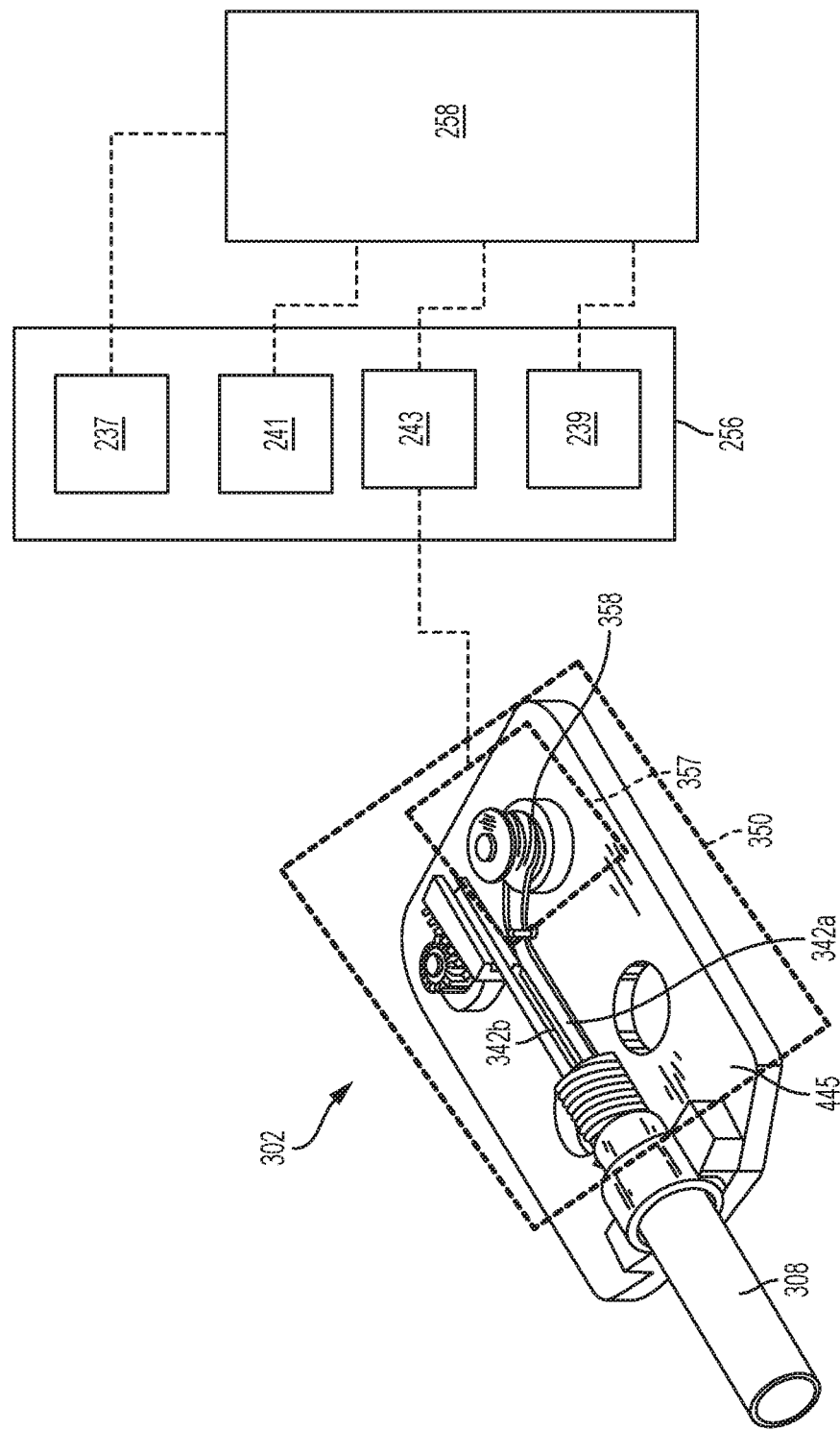
FIG. 5 is a perspective, partially schematic view of the surgical clip applier of FIG. 4 with a portion of the housing removed and showing a drive system of the surgical tool being coupled to motors that are operably coupled to a control system.

The articulation assembly can be operably coupled to an articulation drive assembly 357 of the drive system 350. The articulation drive assembly 357 can translate force from a motor to the articulation assembly to articulate the jaw assembly 310. While the articulation drive assembly 357 can have a variety of configurations, in some embodiments, as shown in FIG. 5, the articulation drive assembly 357 can include an articulation spool 359 coupled to the first and second articulation cables 342a, 342b. As shown in FIG. 5, the articulation cables 342a, 342b extend from opposite sides of the articulation spool 359 such that rotation of the articulation spool 359 can shorten one articulation cable, while lengthening the other. As such, when the articulation spool 359 is caused to rotate, one of the articulation cables 342a, 342b are shortened thereby causing articulation of the jaw assembly 310 in a direction corresponding to the shortened articulation cable.

As indicated above, various embodiments of drive and control systems are provided for producing real-time feedback during operation of electrically-powered surgical clip applier devices thereby allowing a surgeon or other user to effectively and accurately use such device. In general, the drive system is operably coupled between at least one motor and at least one actuation assembly, such as the rotation assembly, the articulation assembly, the jaw closure assembly, and/or the firing assembly. The control system is operably coupled to the at least one motor and is configured to actuate the at least motor to drive the drive system and thereby control movement and operations of the various actuation assemblies, i.e., the rotation assembly, the articulation assembly, the jaw closure assembly, and/or the firing assembly. We discuss the motors, the drive system, the actuation assemblies, and the control system in more detail below.

Motors

As indicated above, one or more motors can be used to drive the various drive assemblies of the drive system of the surgical device. As discussed above, each drive assembly can include various components, such as one or more gears that receive a rotational force from the motor(s) and that transfer the rotational force to one or more actuation assemblies to cause rotary or linear motion of the drive shaft(s). The motor(s) can be located within the surgical device itself or, in the alternative, coupled to the surgical device such as via a robotic surgical system. Each motor can include a rotary motor shaft that is configured to couple to the one or more drive assemblies of the surgical device so that the motor can actuate the one or more drive assemblies to drive the actuation assemblies and cause a variety of movements and actions of the device.

Exemplary motors for use with the systems disclosed herein are described, for example, in U.S. Pat. Nos. 9,445,816 and 9,585,658 and in U.S. Patent Publication Nos. 2012/0292367, 2013/0325034, and 2015/0209059.

It should be noted that any number of motors can be used for driving any one or more drive assemblies of a surgical device. For example, one motor can be used to actuate two different drive assemblies for causing different motions. In certain embodiments, the drive system can include a shift assembly for shifting the drive system between different modes for causing different actions. A single motor can in other aspects be coupled to a single drive assembly. A surgical device can include any number of drive assemblies and any number of motors for actuating the various drive assemblies. The motor(s) can be powered using various techniques, such as by a battery on the device or by a power source connected directly to the device or connected through a robotic surgical system.

Additional components, such as sensors or meter devices, can be directly or indirectly coupled to the motor(s) in order to determine and/or monitor at least one of displacement of a drive assembly coupled to the motor or a force on the motor during actuation of the drive assembly. For example, a rotary encoder can be coupled to the motor to monitor the rotational position of the motor, thereby monitoring a rotational or linear movement of a respective drive assembly coupled to the motor. Alternatively or in addition, a torque sensor can be coupled to the motor to determine or monitor an amount of force being applied to the motor during device operation. It is also contemplated that other ways to determine or monitor force on the motor can include (i) measuring current though the motor by using a sensor or a meter device; or (ii) measuring differences between actual velocity of the motor or components, which may include a combination of a distance travelled and an expired time, and the commanded velocity In certain embodiments, when the at least one motor is activated, its corresponding rotary motor shaft drives the rotation of at least one corresponding drive assembly in the drive system. The drive assembly is coupled to at least one corresponding drive shaft of an actuation assembly, thereby causing linear and/or rotational movement of the drive shaft. While movement of two or more drive shafts can overlap during different stages of operation of the drive system, each motor can be activated independently from each other such that movement of each corresponding drive shaft does not necessarily occur at the same time or during the same stage of operation.

FIG. 3 illustrates an exemplary embodiment of the drive system 150 contained within the housing 138 of the tool mounting portion 102 of the surgical clip applier 100 shown in FIG. 1. The drive system 150 is shown operatively coupled to a plurality of motors, such as a shaft rotation motor 237 configured to drive the rotation drive assembly thereby actuating the rotation assembly, a clip advancing motor 239 configured to drive the clip advancing drive assembly 154 thereby actuating the clip advancing assembly, and a clip forming motor 241 configured to drive the clip forming drive assembly 156 thereby actuating the clip forming assembly.

Additionally, FIG. 5 illustrates an exemplary embodiment of the drive system 350 contained within the tool mounting portion 302 of the surgical clip applier 300 shown in FIG. 4. As shown in FIG. 5, the drive system 350 includes the articulation drive assembly 357. The articulation assembly 357 is shown operatively coupled to an articulation motor 243 that is configured to drive the articulation drive assembly 357 thereby driving the articulation assembly. Although not illustrated, the tool mounting portion 302 can include any of the drive assemblies (e.g., the shaft rotation drive assembly 152, the clip advancing drive assembly 154 and/or the clip forming drive assembly 156) for actuating any of the actuation assemblies described above with respect to the surgical clip applier 100.

As indicated above, the motors 237, 239, 241, 243 as well as the control system 258 can be disposed within the handle housing, like housing 138 shown in FIG. 1, or can be located outside of the handle housing, such as within a surgical robotic system. Over the years a variety of minimally invasive robotic (or "telesurgical") systems have been developed to increase surgical dexterity as well as to permit a surgeon to operate on a patient in an intuitive manner. Many of such systems are disclosed in the following U.S. Patents, which are each herein incorporated by reference in their respective entirety: U.S. Pat. No. 5,792,135 entitled "Articulated Surgical Instrument For Performing Minimally Invasive Surgery With Enhanced Dexterity and Sensitivity," U.S. Pat. No. 6,132,368 entitled "Multi-Component Telepresence System and Method," U.S. Pat. No. 6,231,565 entitled "Robotic Arm DLUS For Performing Surgical Tasks," U.S. Pat. No. 6,783,524 entitled "Robotic Surgical Tool With Ultrasound Cauterizing and Cutting Instrument," U.S. Pat. No. 6,364,888 entitled "Alignment of Master and Slave In a Minimally Invasive Surgical Apparatus," U.S. Pat. No. 7,524,320 entitled "Mechanical Actuator Interface System For Robotic Surgical Tools," U.S. Pat. No. 7,691,098 entitled "Platform Link Wrist Mechanism," U.S. Pat. No. 7,806,891 entitled "Repositioning and Reorientation of Master/Slave Relationship in Minimally Invasive Telesurgery," and U.S. Pat. No. 7,824,401 entitled "Surgical Tool With Wristed Monopolar Electrosurgical End Effectors." Many of such systems, however, have in the past been unable to generate the magnitude of forces required to effectively cut and fasten tissue.

Control System

Figure 6:
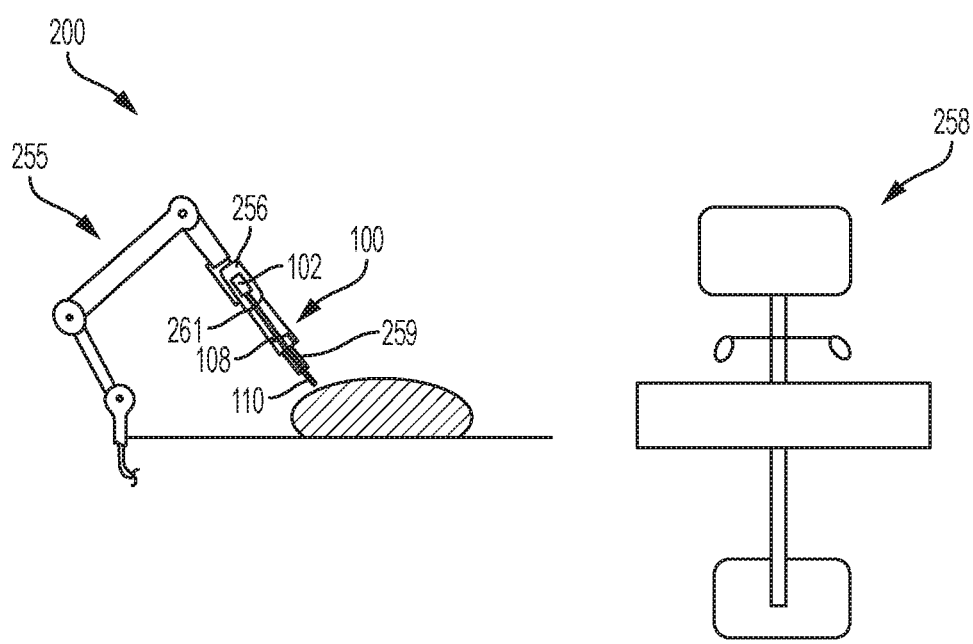
FIG. 6 is a perspective, partially schematic view of an exemplary embodiment of a surgical robotic system that includes a robotic arm having the surgical clip applier of FIG. 1 mounted thereon, and being wirelessly coupled to a control system.

FIG. 6 illustrates an exemplary embodiment of surgical robotic system 200 that includes a robotic arm 255 that is wirelessly coupled to a control system 258 having a console with a display and two user input devices. One or more motors, such as the motors 237, 239, 241, 243 shown in FIGS. 3 and 5, are disposed within a motor housing 256 that is coupled to an end of the robotic arm 255. The tool mounting portion 102 of the surgical clip applier 100 is configured to be seated within the motor housing 256 and the interface 140 on the tool mounting portion 102 functions to mechanically and electrically couple the drive system 150 in the tool mounting portion 102 to the motors within the motor housing 256. As a result, when the motor(s) are activated by the control system 258, the motor(s) can actuate the drive system 150 in the surgical clip applier 100. As shown in FIG. 6, the elongate shaft assembly 108 extends from the tool mounting portion 102. During surgery, the elongate shaft assembly 108 can be placed within and extend through a trocar 259 that is mounted on the bottom of a carrier 261 extending between the motor housing 256 and a trocar support. The carrier 261 allows the surgical clip applier 100 to be translated into and out of the trocar 259. Although the surgical clip applier 100 is shown in FIG. 6, the surgical clip applier 300, shown in FIG. 4, can be used within the surgical robotic system 200 in a similar manner.

As discussed above, the control system 258 and motor(s) can power and control various actuation assemblies of the surgical clip appliers 100, 300, such as the rotation assembly, the clip advancing assembly, the clip forming assembly, and the articulation assembly. Unlike manually-operated devices, electrically-powered surgical devices can lack control and tactile feedback, thereby reducing a surgeon's ability to effectively, accurately, and safely use these devices. Further, manually-operated devices are typically displacement controlled in which mechanical hard stops are used to control displacement of the various drive assemblies. However, using mechanical stops in an electrically-powered device has its disadvantages. For example, a user can be limited in assessing whether a jam has occurred in the device or if the clip has been fully formed in tissue.

Referring to FIGS. 3 and 5, as discussed above, the motors 237, 239, 241, 243 can be operably coupled to respective drive assemblies 152, 154, 156, 357, which can be coupled to respective actuation assemblies of the elongate shaft assemblies 108, 308. In order to drive the actuation assemblies, the motors 237, 239, 241, 243 can be operably coupled to the control system 258 such that the control system can control the motors 237, 239, 241, 243. As described above, one or more motors can be coupled to a rotary encoder that provides linear and/or rotary displacement information to the control system 258. Such displacement information can be used by the control system 258 to appropriately control one or more of the drive assemblies to thereby control associated actuation assemblies. Alternatively or in addition, the one or more motors can be coupled to a corresponding torque sensor that provides the control system 258 with information about the amount of force being applied to the motor(s) during operation of the drive systems 150, 350, which can also be used by the control system 258 to appropriately control one or more of the drive assemblies to thereby control associated actuation assemblies.

The control system 258 can communicate with the motors using various techniques, such as via a direct wired connection or using wireless communication. Various wireless communication embodiments are described in U.S. patent application Ser. No. 13/118,259 to James R. Giordano et al. filed on May 27, 2011, the disclosure of which is herein incorporated by reference in its entirety.

Operation of Control System

Generally, the control system can control movement and actuation of a surgical device. For example, the control system can include at least one computer system and can be operably coupled to the at least one motor that drives a drive system on the surgical device. The computer system can include components, such as a processor, that are configured for running one or more logic functions, such as with respect to a program stored in a memory coupled to the processor. For example, the processor can be coupled to one or more wireless or wired user input devices ("UIDs"), and it can be configured for receiving sensed information, aggregating it, and computing outputs based at least in part on the sensed information. These outputs can be transmitted to the drive system of surgical device to control the surgical device during use.

In certain embodiments, the control system can be a closed-loop feedback system. The stored data within the computer system can include predetermined threshold(s) for one or more stages of operation of the drive system. When the control system is actuated, it drives one or more motors on or coupled to the surgical device, consequently actuating the drive system through each stage of operation. During each stage of operation, the control system can receive feedback input from one or more sensors coupled to the motor(s) that sense speed, displacement, and/or torque of the motor(s). The computer system can aggregate the received feedback input(s), perform any necessary calculations, compare it to the predetermined threshold for the corresponding stage of operation, and provide output data to the motor(s). If at any time during each stage of operation the control system determines that the received input exceeds a maximum predetermined threshold or is less than a minimum predetermined threshold, the control system can modify the output data sent to the motor based on the programmed logic functions. For example, the control system can modify the output data sent to the motor(s) to reduce a current delivered to the motor to reduce motor force or a voltage delivered to the motor to thereby reduce a rotational speed of the motor(s) or to stop movement of the motor(s).

A person skilled in the art will appreciate that, while control systems are shown and described below with respect to drive systems configured for applying a clip to tissue, the control systems disclosed herein can be coupled to drive systems that are configured for other surgical devices, such as staplers, forceps/graspers, needle drivers, scissors, electrocautery tools, clip removers, suction tools, irrigation tools, etc.

Various exemplary control systems for controlling various drive assemblies and actuation assemblies are discussed in detail below. A surgical clip applier system can utilize any one or more of the techniques for controlling a surgical clip applier device.

Load Thresholds based on Cam Displacement

As discussed above, a cam of the surgical clip applier can be distally advanced along the jaws to cause the jaws to close and form a clip positioned therebetween, such as the cam 134 and jaws 112, 114 of clip applier 100 illustrated in FIG. 2. During such jaw closure and clip formation, the cam is advanced a first distance to approximate the distal ends of the jaws, which includes causing the distal ends of the jaws to almost or completely touch, and is referred to herein as a jaw tips approximation step. After being advanced the first distance, the cam is then advanced a second distance to cause the jaws to fully close and form the clip positioned therebetween, which is referred to herein as a complete jaw closure step. After the cam has advanced the second distance, thus completing the complete jaw closure step, the cam can be proximally retracted to open the jaws thereby releasing the clip formed in tissue. Various issues can arise during the jaw tips approximation step and the complete jaw closure step that can cause damage to either the jaws or tissue. For example, during the jaw tips approximation step, an object other than the clip intending to be formed between the jaws (e.g., another clip) can accidentally be positioned between the jaws. Such other object can interfere with proper clip formation and can cause damage to the jaws and surgical errors. For example, the cam can attempt to force the jaws closed with the other object positioned therebetween, thereby causing the jaws to deform and ineffectively form clips. Furthermore, during the complete jaw closure step, too much force can be applied to the jaws to form the clip thereby causing unwanted cutting of the tissue between the jaws. The control system described herein can thus be configured to monitor force loads for advancing the cam and, based on such force monitoring, control movement of the cam to prevent damage to the jaws during the jaw tips approximation step and prevent damage to the tissue during the complete jaw closure step, as described in greater detail below.

Figure 7:
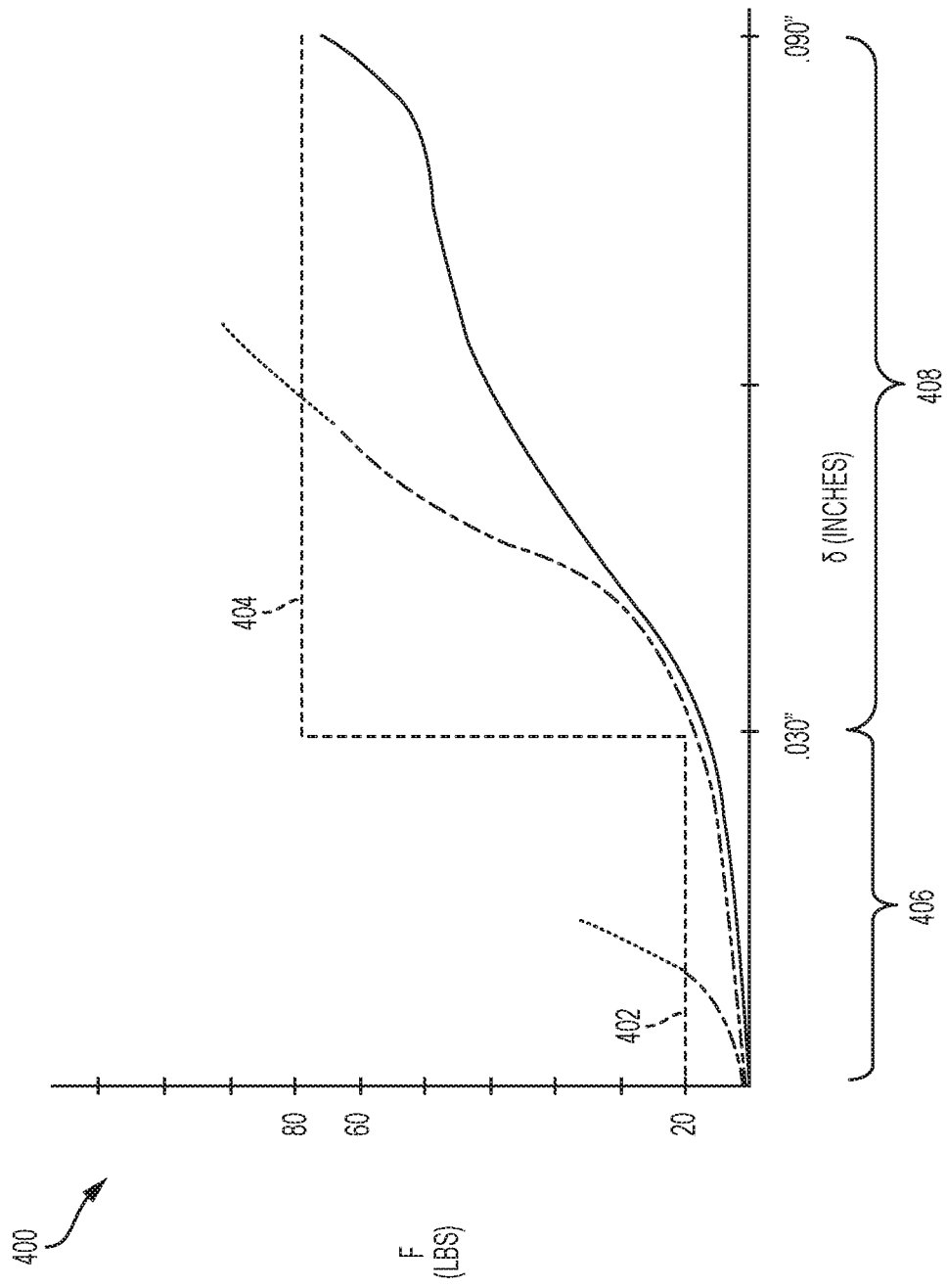
FIG. 7 is a graph showing force as a function of displacement of a jaw closure assembly, including two different force thresholds at different stages of closure.

FIG. 7 illustrates a jaw closure thresholds graph 400 with the x-axis including a measured displacement (e.g., inches) of the cam and the y-axis including a measured torque or force (e.g., pounds) applied to the cam to cause the cam to distally advance and close the jaws for forming a clip positioned therebetween. The control system 258 includes a first predefined threshold 402 and a second predefined threshold 404, with the first threshold 402 being associated with a smaller force (e.g., approximately 20 pounds) than the second threshold 404 (e.g., approximately 80 pounds). The first threshold 402 can be applied to the jaw tips approximation step that occurs during advancement of the cam along a first distance 406 (e.g., 0.030 inch) to move the jaws from the open position to where the distal tips of the jaws are approximated. The second threshold 404 can be applied to the complete jaw closure step that occurs during advancement of the cam along the second distance 408 (e.g., 0.060 inch) to move the jaws into the fully closed position thereby fully forming a clip positioned therebetween.

For example, the control system 258 can monitor the force loads to advance the cam along the first distance 406 and it can compare such force loads to the first threshold 402. The first threshold 402 can be set to a force value that, if exceeded, indicates that an object other that the clip intending to be formed is positioned between the jaws. As such, if the first threshold 402 is exceeded, the control system 258 at least stops advancing the cam and can optionally retract the cam to allow the jaws to open. For example, the first threshold 402 can be associated with a low enough force such that if a foreign object is positioned between the jaws, the control system will stop advancing the cam before damage to the jaws occurs.

After the control system has advanced the cam the first distance 406 without the measured force loads exceeding the first threshold 402, the control system assumes that a foreign object is not positioned between the jaws. The control system then monitors force loads required to advance the cam along the second distance 408 and compares such force loads to the second threshold 404. The second threshold 404 is greater than the first threshold 402 due to the expected greater forces required to fully close the jaws and form the clip to tissue. However, the second threshold 404 is associated with a low enough force to prevent the jaws and/or clip from shearing the tissue positioned therebetween. If a measured force load exceeds the second threshold 404 during advancement of the cam along the second distance 408, the control system at least stops advancing the cam to thereby prevent shearing of the tissue. As such, the control system 258 can apply different thresholds along two different stages of jaw closure and clip formation (e.g., jaw tips approximation step and complete jaw closure step) to prevent force loads applied to the cam that can result in either damage to the jaws or tissue, thereby improving longevity of the surgical clip applier and reducing surgical errors.

Cam Displacement Control Based on Velocity and Load

As discussed above, the control system can monitor and adjust forces applied to the cam based on the position of the cam, such as based on whether the cam is advancing during the jaw tips approximation step or the complete jaw closure step. In addition to monitoring forces, some embodiments of the control system can monitor and control a velocity of distal advancement of the cam during the jaw tips approximation step or the complete jaw closure step, as will be discussed in greater detail below. Such monitoring and control of cam travel velocity can assist the control system with controlling forces applied to the cam to ensure such applied forces do not exceed a predefined threshold (e.g., first or second predefined thresholds 402, 404 shown in FIG. 7) thereby protecting the jaws from damage.

Figure 8:
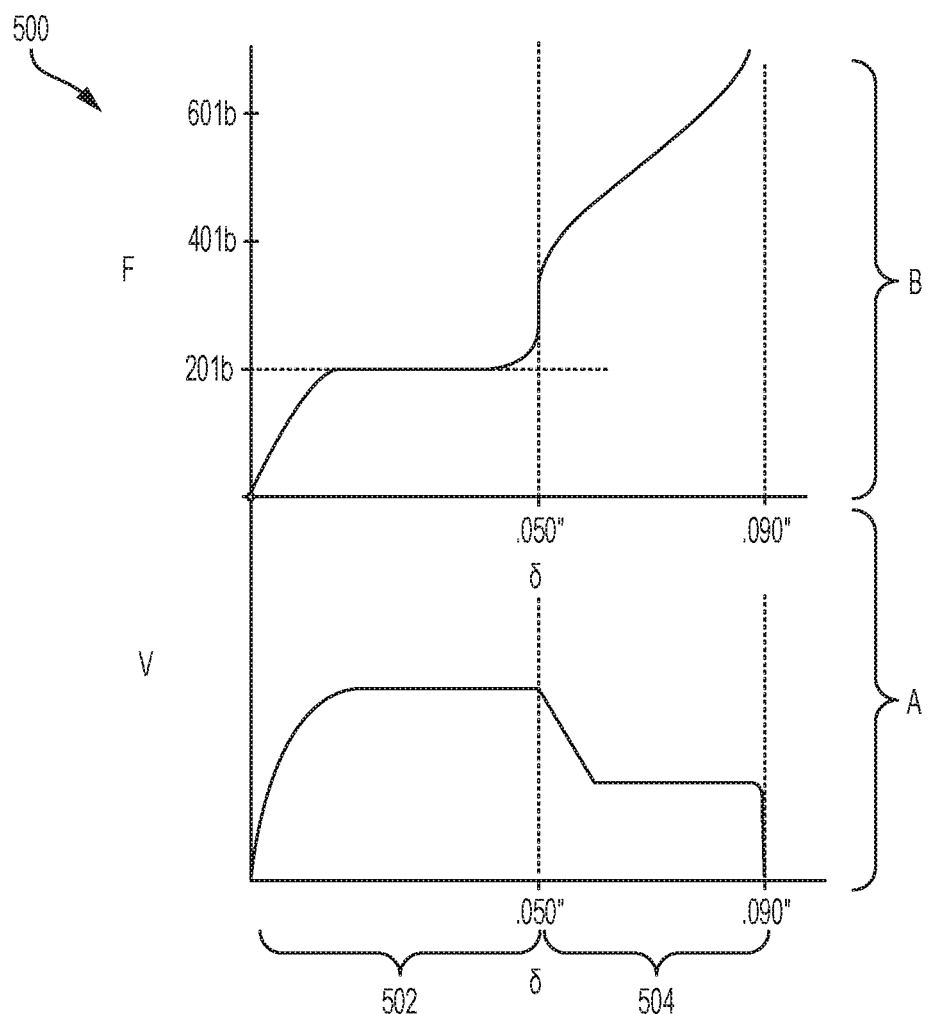
FIG. 8 is a graph showing velocity as a function of displacement of a jaw closure assembly in section A, and showing force as a function of displacement of a jaw closure assembly in section B.

FIG. 8 illustrates a jaw closure control graph 500 including a section A that shows a velocity (e.g., indicated along y-axis of section A) of distal advancement of the cam (e.g., indicated along x-axis of section A) during the jaw tips approximation step, which can occur as the cam advances along a first distance 502 (e.g., 0.05 inches). Section A of the jaw closure control graph 500 also shows the velocity of distal advancement of the cam during the complete jaw closure step, which can occur as the cam advances along a second distance 504 (e.g., 0.04 inches). Section B of the jaw closure control graph 500 shows a measured force or torque (e.g., pounds), as indicated along a y-axis of section B, applied to the cam to cause the cam to distally advance (e.g., indicated along x-axis of section B) and close the jaws for forming a clip positioned therebetween.

As shown in section A of FIG. 8, the control system 258 can control the cam to advance the cam at a greater velocity along the first distance 502 (e.g., up until the distal ends of the jaws approximate) compared to when the cam advances along the second distance 504 (e.g., up until the jaws fully close and clip is fully formed therebetween). For example, a slower speed of distal advancement is preferred along the second distance 504 compared to the first distance 502 due to relatively higher forces being applied to the cam (e.g., approximately 40 pounds to 80 pounds) during distal advancement of the cam to fully close the jaws and form the clip compared to along the first distance 502 for approximating the distal ends of the jaws (e.g., approximately 20 pounds). As such, the control system 258 assists in preventing damage to the jaws during application of the higher loads along the second distance 504 by slowing down the distal advancement speed of the cam. Furthermore, the control system 258 allows for faster cam advancement along the first distance 502 due to relatively lower forces required to advance the cam along the first distance 502 for approximating the distal ends of the jaws.

For example, the control system 258 can control the velocity of distal advancement of the cam along the first distance 502 while still monitoring the forces applied to the clip advancing motor 239 to ensure the force loads do not exceed a predetermined threshold (e.g., the first predefined threshold 402 along the first distance 406 shown in FIG. 7). Once the distal tips are approximated (e.g., after the cam has traveled the first distance 502), the control system can reduce the speed of distal advancement of the cam, such as reduce the speed by half or more, until the clip is fully formed between the jaws (e.g., after the cam has traveled the second distance 504), at which time the control system can stop advancing the cam. During distal advancement of the cam along the second distance 504, the control system can continue to monitor the forces applied to the clip advancing motor 239 to ensure the forces do not exceed a predetermined threshold (e.g., the second predefined threshold 404 along the second distance 408 shown in FIG. 7). As such, although the control system can control the cam to advance at a predefined speed depending on a displacement position of the cam, the control system is configured to adjust the speed and/or direction of displacement of the cam, including stopping travel and retracting the cam, based on measured forces applied to the clip advancing motor 239. This can allow the control system to efficiently close the jaws and form a clip therebetween while also protecting the jaws from damage.

Cam Displacement Control Based on Articulation

Articulation of the jaw assembly of the surgical clip applier can require greater forces to distally advance the cam compared to when the jaw assembly is not articulated. For example, additional forces can be needed to advance either the cam or a component that advances the cam along the articulation region (e.g., such as the articulation region 341 illustrated in FIG. 4) during articulation of the jaw assembly compared to when the articulation region is straight (e.g., no articulation of the jaw assembly). Furthermore, other changes in required forces for actuating the surgical clip applier can be needed as a result of articulation of the jaw assembly. As such, some embodiments of the control system can be configured to monitor articulation of the jaw assembly and, based on the monitored articulation, adjust one or more of an applied force and a threshold for controlling actuation of one or more actuation assemblies of the surgical clip applier, as will be described in greater detail below. Such adjusting of applied forces and/or thresholds can protect the surgical clip applier device from damage as well as ensure efficient and effective performance of the surgical clip applier, including the applying of clips to tissue.

Figure 9:
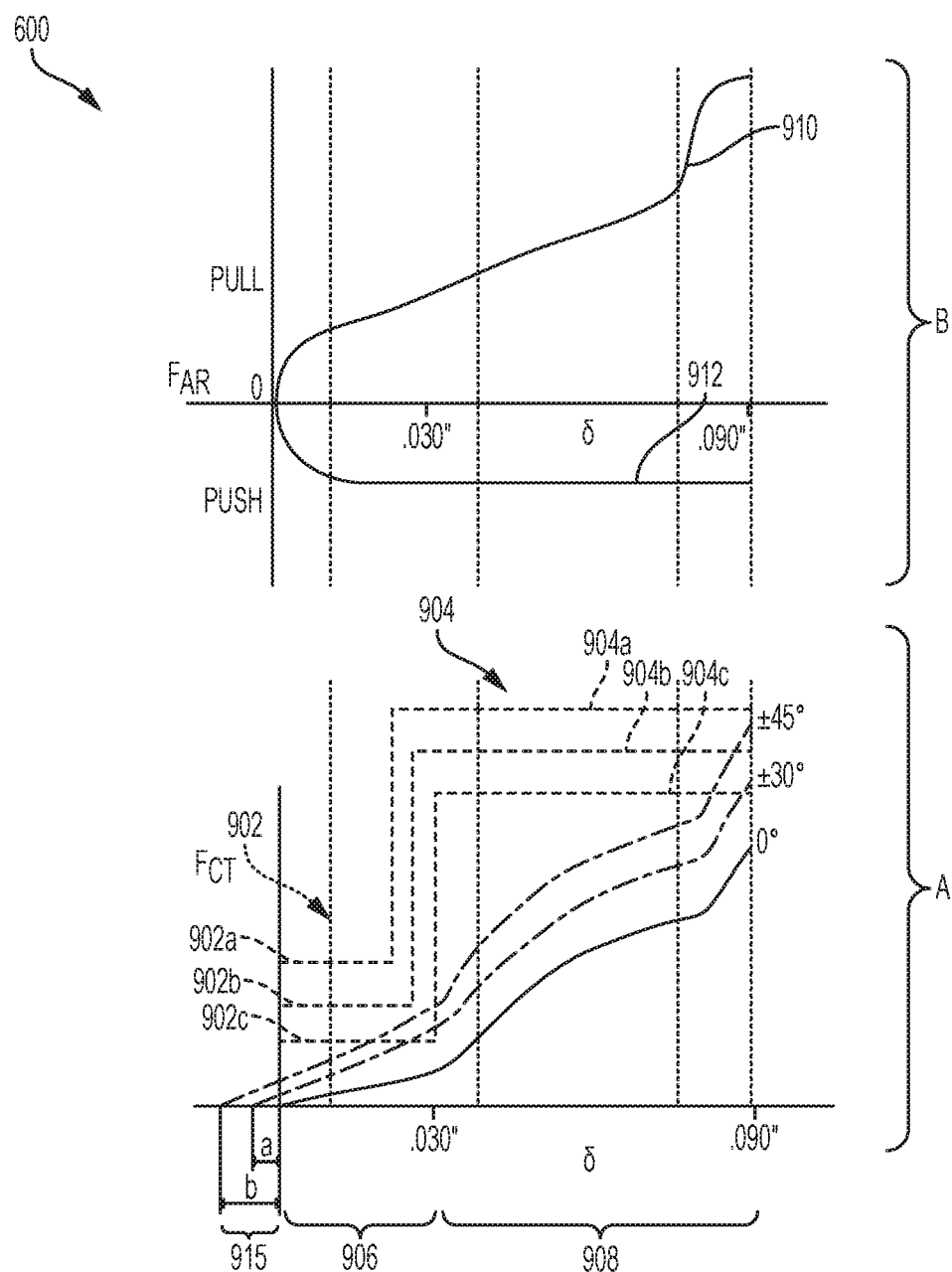
FIG. 9 is a graph showing force as a function of displacement of a cam of a jaw closure assembly in section A, and showing force as a function of displacement of articulation cables as the cam is advanced distally to maintain articulation of the jaw assembly in section B.

FIG. 9 illustrates an articulation force control graph 600 including a section A with the x-axis including a measured displacement (e.g., inches) of the cam of the surgical clip applier (e.g., such as cam 134 of clip applier 100 illustrated in FIG. 2) and the y-axis including a measured torque or force (e.g., pounds) applied to the cam to cause the cam to distally advance and close the jaws for forming a clip positioned therebetween. Similar to what is described above with respect to FIG. 7, the control system 258 can apply different thresholds as the cam advances along a first distance 906 (e.g., the jaw tips approximation step) compared to as the cam advances along a second distance 908 (e.g., the complete jaw closure step). The different thresholds can prevent force loads applied to the cam that can result in either damage to the jaws or tissue, thereby improving longevity of the surgical clip applier and reducing surgical errors.

For example, as shown in section A of FIG. 9, a first threshold 902 can be applied to the jaw tips approximation step that occurs during advancement of the cam along the first distance 906 (e.g., approximately 0.030 inch) to move the jaws from the open position to when the distal tips of the jaws are approximated. Furthermore, a second threshold 904 can be applied to the complete jaw closure step that occurs during advancement of the cam along the second distance 908 (e.g., approximately 0.060 inch) to move the jaws into the fully closed position thereby fully forming a clip positioned therebetween. As shown in section A in FIG. 9, the force values associated with the first and second thresholds 902, 904 increase as articulation increases (e.g., an articulation angle increases). The articulation angle can be defined, for example, as an angle formed between a longitudinal axis of the jaw assembly and a longitudinal axis of the shaft.

For example, as shown in section A of FIG. 9, the first threshold 902a at a 45 degree articulation angle can be greater than the first threshold 902b at a 30 degree articulation angle, which can be greater than the first threshold 902c at a zero degree articulation angle. Similarly, the second threshold 904a at a 45 degree articulation angle can be greater than the second threshold 904b at a 30 degree articulation angle, which can be greater than the second threshold 904c at a zero degree articulation angle. The control system 258 can increase the first and second thresholds 902, 904 as the articulation angle increases to account for the increased loads to be expected to drive the cam distally, as discussed above. Furthermore, the control system increases the first and second thresholds 902, 904 to load values that account for the increase in force to advance the cam during articulation while also ensuring that any applied force loads below the first and second thresholds 902, 904 do not damage either the jaws or the tissue. Such adjusting of the first and second thresholds 902, 904 can prevent the control system from detecting forces that exceed either the first or second threshold 902, 904 when such exceeded forces are attributed to the additional forces required to advance the cam during articulation, which would result in unnecessarily slowing down or stopping advancement of the cam.

For example, as described above with respect to FIG. 7, the first threshold 902 is set to a force value that, if exceeded, indicates that an object other that the clip intending to be formed is positioned between the jaws. As such, if the first threshold 902 is exceeded, the control system 258 at least stops advancing the cam and can retract the cam to allow the jaws to open. The control system can then monitor force loads required to advance the cam along the second distance 908 and compare such force loads to the second threshold 904. The second threshold 904 is greater than the first threshold 402 due to the expected greater forces required to fully close the jaws and form the clip to tissue. However, the second threshold 904 is associated with a low enough force to prevent the jaws and/or clip from shearing the tissue positioned therebetween. If a measured force load exceeds the second threshold 904 during advancement of the cam along the second distance 908, the control system at least stops advancing the cam to thereby prevent shearing of the tissue. As such, the control system 258 can apply different thresholds (e.g., first and second thresholds 902, 904) along two different stages of jaw closure and clip formation (e.g., jaw tips approximation step and complete jaw closure step) to prevent force loads applied to the cam that can result in either damage to the jaws or tissue, as well as adjust (e.g., increase or decrease) the thresholds based on articulation of the jaw assembly to thereby prevent damage to the surgical clip applier and reduce surgical errors.

Articulation of the jaw assembly can also cause a change in length and/or positioning of one or more components of the shaft assembly, including the clip forming assembly. For example, as the articulation angle increases, the cam can be caused to distally advance or proximally retract as a result of the clip forming assembly bending along the articulation region. As such, the control system can shift the first and second thresholds 902, 904 such that they at least begin at a more proximal or distal position to accommodate at least the changed length and/or positioning of the clip forming assembly. For example, as shown in section A in FIG. 9, as the articulation angle increases, the cam can be increasingly proximally retracted along an offset distance 915. To compensate for such increasing proximal retraction along the offset distance 915 the control system can increasingly shift the end of the first distance 906 and start of the second distance 908, thereby increasingly shifting proximally the point at which the control system stops applying the first threshold 902 and starts applying the second threshold 904.

Another applied force that can change due to articulation of the jaw assembly can include push and/or pull forces associated with the articulation cables of the articulation assembly (e.g., such as the first and second articulation cables 342a, 342b of clip applier 300 illustrated in FIG. 4) that control articulation about the articulation region. For example, pull forces of one of the first and second articulation cables to cause articulation can change as the cam distally advances to close the jaws and form the clip, as will be discussed in greater detail below.

Section B of FIG. 9 shows corresponding pull forces 910 and push forces 912 (e.g., indicated along the y-axis) as the cam is advanced distally along the first and second distances 906, 908 (e.g., indicated along the x-axis of both section A and B). As discussed above, to articulate the jaw assembly, one of the articulation cables is pulled to cause articulation associated with the pulled articulation cable (e.g., pulling of a first articulation cable 342a can cause articulation of the jaw assembly to the left). As shown in section B, as the cam is advanced distally, greater forces are required to maintain articulation of the jaw assembly, including maintaining a same articulation angle throughout distal advancement of the cam. As such, the control system can adjust the forces applied to the articulation assembly as the cam distally advances to ensure that the jaw assembly maintains an articulation angle throughout the distal advancement of the cam (e.g., along the first and second distances 906, 908). Such maintaining of the articulation angle can ensure that the jaws of the jaw assembly are not moved during jaw closure and clip formation, which could adversely affect the ability of the surgical clip applier to properly apply a clip at an intended tissue target. Thus, such modifying of forces to the articulation assembly by the control system based on cam advancement can reduce procedure time and surgical errors.

Clip Loading Control

The clip advancing assembly is another actuation assembly of the surgical clip applier that can cause surgical errors and/or damage to either a clip or the surgical clip applier if caused to improperly advance or if too great of a force is applied to the actuation assembly. For example, in one aspect, the clip advancing assembly is configured to advance a distal-most clip into the jaws for allowing the jaws to form the clip to tissue. The clip advancing assembly includes at least one clip advancing component (e.g., such as the feed bar 128 and advancer assembly 130 of clip applier 100 illustrated in FIG. 2) that is configured to advance the distal-most clip into the jaws during actuation of the clip advancing assembly. For example, if such clip advancing component is advanced at too great of a speed as the clip approaches a distal end of the jaws (e.g., where the clip is properly positioned for forming between the jaws), the clip can be ejected from the distal end of the jaws and thus not properly placed for forming between the jaws. Additionally, such ejecting of the clip from the jaws can result in surgical errors and prolonged procedure time, particularly if the clip is ejected into the patient. As such, some embodiments of the control system are configured to monitor at least a position of the clip advancing component for controlling a velocity of distal advancement of the clip advancing component to ensure a distal-most clip is not ejected from the jaw assembly and is properly placed in the distal end of the jaws for being applied and formed to tissue, as will be described in greater detail below.

Figure 10:
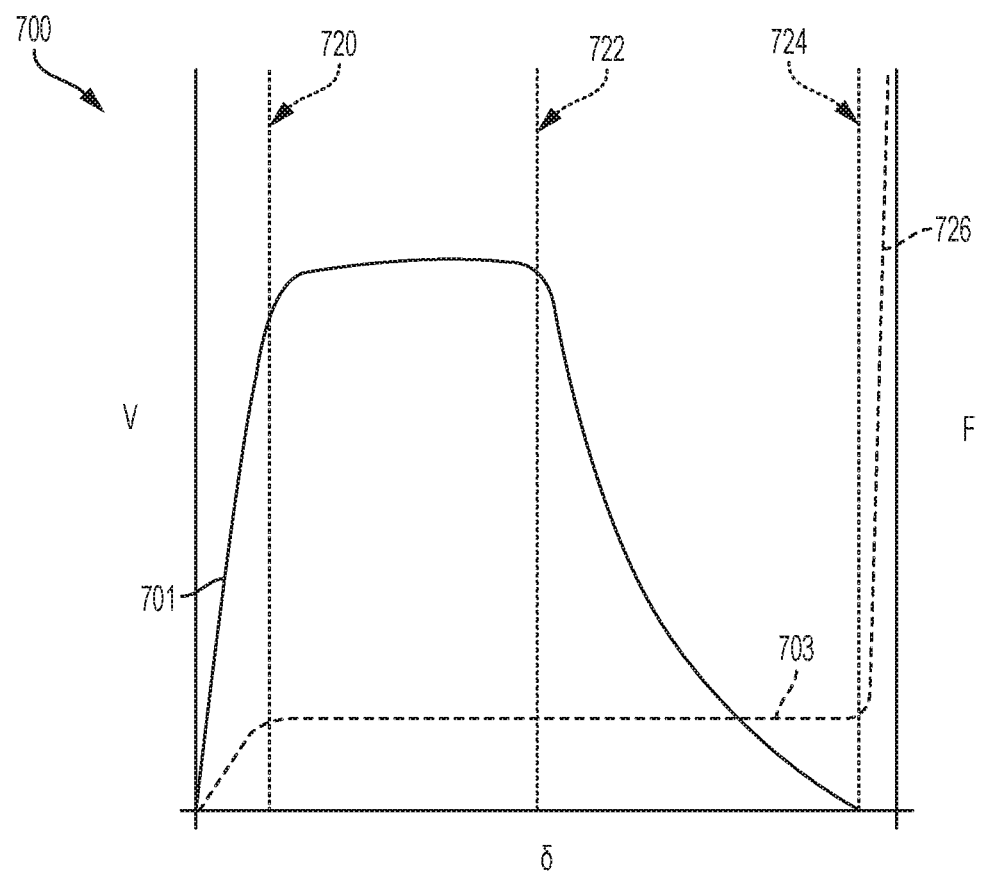
FIG. 10 is a graph that shows measured and controlled velocities of a clip advancing component and measured forces applied to the clip advancing component as a function of displacement of the clip advancing component.

FIG. 10 illustrates a clip advancing control graph 700 that shows measured and controlled velocities (e.g., shown as velocity line 701) of the clip advancing component, as indicated along the y-axis, as the clip advancing component is advanced distally, as indicated along the x-axis, such as during loading of a distal-most clip into the jaws. As shown in FIG. 10, the control system can cause the clip advancing component to advance at a much higher velocity between a first position 720 where the clip advancing component engages the distal-most clip for loading into the jaws and a second position 722 where the clip advancing component has partially advanced the clip into the jaws, e.g., approximately ¾ of the total distance into the jaws. Between the second position 722 and a third position 724 where the clip is properly loaded in the distal end of the jaws, the control system can reduce the velocity of advancement of the clip advancing component, including stopping advancement of the clip advancing component when the clip advancing component reaches the third position 724, as shown in FIG. 10. Such reduction and stopping of advancement velocities between the second and third positions 722, 724 can ensure the clip being loaded into the jaws does not get advanced too quickly and is therefore not caused to be ejected or damaged.

In some embodiments, a distal end of the jaws can include a stop feature that is configured to allow the clip being loaded into the jaws to mate there against for assisting with properly positioning the clip between the jaws (e.g., at the third position 724). Such stop feature can thus assist with properly positioning the loaded clip between the jaws, such as for clip formation to tissue, however, the stop feature can damage the clip and/or insufficiently stop further distal advancement if the clip is advanced into the stop feature at too great of a velocity. As such, the control system can prevent such damage to the clip and ensure proper positioning of the clip between the jaws, including embodiments that include a stop feature, by reducing the velocity to a stop by the time the clip is properly positioned between the jaws (e.g., the clip advancing component reaches the third position 724).

As shown in the clip advancing control graph 700 in FIG. 10, the control system can also monitor a force applied to the clip advancing component (e.g., shown as force line 703) and can compare such monitored forces against at least one predefined force threshold (not shown). For example, if the monitored forces exceed a predefined force threshold, the control system can determine that there is an error associated with the clip advancing drive assembly, such as an object impeding advancement of the clip into the jaws. When the control system detects an exceeded force threshold, the control system can adjust the velocity of the clip advancing component, including stopping advancement of the clip advancing component, to ensure that a clip and/or the surgical clip applier device does not get damages and that a clip is not ejected from the jaw assembly. Furthermore, as shown in FIG. 10, a force spike 726 is expected as the clip contacts the stop feature. However, the control system can control the extent of the force spike 726, and thus prevent clip ejection, by reducing the velocity of advancement of the clip advancing component, including stopping advancement, as the clip advancing component advances to the third position 724, as shown in FIG. 10. As such, the control system can monitor and control velocities and applied forces associated with advancing the clip advancing component to ensure a clip is properly positioned within the jaws and prevent damage to either the clip or the surgical clip applier.

Clip Stack Advancement Control

As discussed above, the actuation assembly of the surgical clip applier can cause surgical errors and/or damage to either a clip or the surgical clip applier if caused to improperly advance or if too great of a force is applied to the actuation assembly. For example, in another aspect, the clip advancing assembly is configured to advance a clip-stack distally after a distal-most clip is removed from the clip stack, such as for loading between the jaws. Furthermore, the clip advancing assembly is configured to advance the clip stack distally to advance a next distal-most clip into a distal loading position. For example, properly positioning the next distal-most clip into the distal loading position can allow the next distal-most clip to be appropriately removed from the clip stack for loading into the jaws The clip advancing assembly includes at least one clip-stack advancing component (e.g., such as the feeder shoe 124 of clip applier 100 illustrated in FIG. 2) that is configured to distally advance the clip stack during actuation of the clip advancing assembly. If such clip-stack advancing component is advanced at too great of a speed as the next distal-most clip approaches the distal loading position, the clip stack can be ejected from the distal end of the jaws, which can result in surgical errors and prolonged procedure times. Damage to either the clips or the surgical clip applier can also result. Furthermore, a jam that prevents the clip stack from advancing can also result in such damage and errors if the clip-stack advancing component attempts to advance the clip stack while being prevented from doing so. As such, in some embodiments, the control system is configured to monitor at least a position of the clip-stack advancing component for controlling at least one of a velocity of the clip advancing component and a force applied to the clip-stack advancing component to ensure the clip stack is properly advanced and the next distal-most clip is safely positioned in the distal loading position, as will be described in greater detail below.

Figure 11:
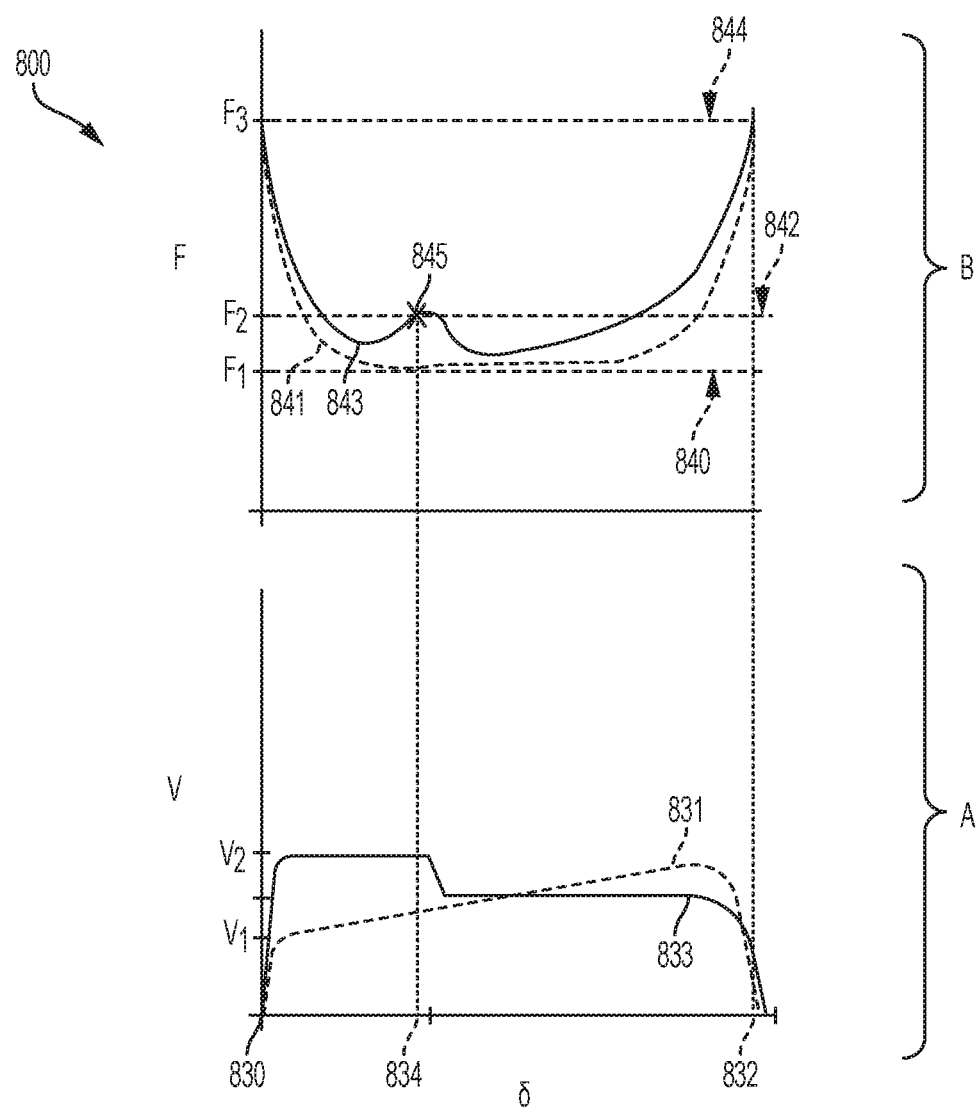
FIG. 11 is a graph showing in section A measured and controlled velocities of a clip-stack advancing component as the clip-stack advancing component and clip stack is advanced distally, and showing in section B measured forces applied to the clip-stack advancing component during distal advancement.

FIG. 11 illustrates a clip-stack advancing control graph 800 including a section A that shows measured and controlled velocities of the clip-stack advancing component, as indicated along the y-axis, as the clip-stack advancing component is advanced distally, as indicated along the x-axis, such as during distal advancement of the clip stack for positioning the next distal-most clip in the distal loading position. Section B of the clip-stack advancing control graph 800 shows measured and controlled force loads applied to the clip-stack advancing component, as indicated along the y-axis, as the clip-stack advancing component is advanced distally, as indicated along the x-axis. For example, as shown in FIG. 11, under normal conditions where no interference (e.g., an object or mechanical jam) occurs during distal advancement of the clip stack, the control system causes the clip-stack advancing component to mostly advance at a slightly increasing or steady velocity (e.g., shown as first velocity line 831) between a first clip-stack position 830 where the clip-stack advancing component begins to distally advance the clip stack and a second clip-stack position 832 where the clip-stack advancing component has advanced the next distal-most clip into the distal loading position. Furthermore, as shown, in section A, the control system significantly reduces the velocity of the clip-stack advancing component, including stopping advancement, as the clip-stack advancing component approaches and reaches the second clip-stack position 832. Such control of velocities between the first and second clip-stack positions 830, 832 can ensure the clip stack is efficiently advanced yet not advanced too quickly as the next distal-most clip approaches the distal loading position, thereby preventing damage to the device and/or ejection of the clip stack.

As shown in section B, the forces applied to the clip-stack advancing component can also be monitored and controlled by the control system 258 to prevent damage to the surgical clip applier and/or clip stack. Furthermore, the control system can include one or more force thresholds that the control system can compare measured applied forces against for detecting any interferences affecting clip-stack advancement, and it can adjust a velocity of the clip-stack advancing component accordingly. For example, as shown in section B in FIG. 11, the control system can include a first force threshold 840 and a second force threshold 842 that define lower and upper force boundaries, respectively, that the measured forces associated with advancing the clip-stack advancing component are expected to fall within. Furthermore, the control system can include a third force threshold 844 that can define a maximum allowed measured force as the clip-stack advancing component begins to advance the clip stack and as the clip-stack advancing component approaches the second position 832 where the next distal-most clip is positioned in the distal loading position. Section B shows an example first force line 841 under normal conditions where an interference does not interfere with distal advancement of the clip stack. As such, the measured force remains between the first and second force thresholds 840, 842 aside from expected higher measured forces when the clip stack is first advanced (e.g., overcoming friction) and when the next distal-most clip is positioned in the distal loading position (e.g., the next distal-most clip mates against a distal retainer that properly positions the next distal-most clip in the distal loading position). In such a scenario, the control system can allow the clip-stack advancing component to have a velocity profile similar to the first velocity line 831, as described above and shown in section A.

As shown in section B, if the control system detects a measured force that exceeds the second force threshold (e.g., at an interference force point 845 along a second force line 843), the control system can sharply reduce the velocity, as shown in the second velocity line 833 in section A (e.g., when the clip-stack advancing component is in a third position 834). Such sharp reduction in velocity can allow the force to decrease and can allow subsequent force measurements to be within the first and second force thresholds 840, 842 until the clip-stack advancing component approaches and reaches the second position 832. As such, the control system can adjust the velocity of the clip-stack advancing component to adjust the force applied to advance the clip stack, including stopping advancement of the clip-stack advancing component if lower velocities do not return measured force values between the first and second thresholds 840, 842. By monitoring the position of the clip-stack advancing component and force measurements applied to the clip-stack advancing component and adjusting the velocity of the clip-stack advancing component based on such monitoring, the control system can ensure the clip stack is properly advanced and the next distal-most clip is appropriately positioned in the distal loading position, thereby preventing damage to the device and/or ejection of the clip stack.

Impedance Based on Stage of Clip Formation

As an alternative to measuring and monitoring forces applied to a motor, such as for determining a displacement of a component of the surgical clip applier, some embodiments of the control system can measure and monitor an impedance or current through one or more motors and/or various other components of the surgical clip applier. For example, such measured impedance or current can be used by the control system for determining a displacement or positioning of one or more components of the surgical clip applier.

In some embodiments, the control system can be configured to measure and monitor impedance through a jaw assembly of a surgical clip applier. For example, the jaw assembly can include jaws for positioning and forming a clip positioned therebetween. As will be described in greater detail below, the control system can monitor an impedance or current through the jaw assembly for assisting with properly positioning tissue between the jaws to ensure proper clip formation in and/or around the tissue. For example, improper placement of the tissue relative to the jaws can result in ineffective application of the clip to the tissue, which can result in surgical errors and prolonged surgical procedures.

Figure 12A:
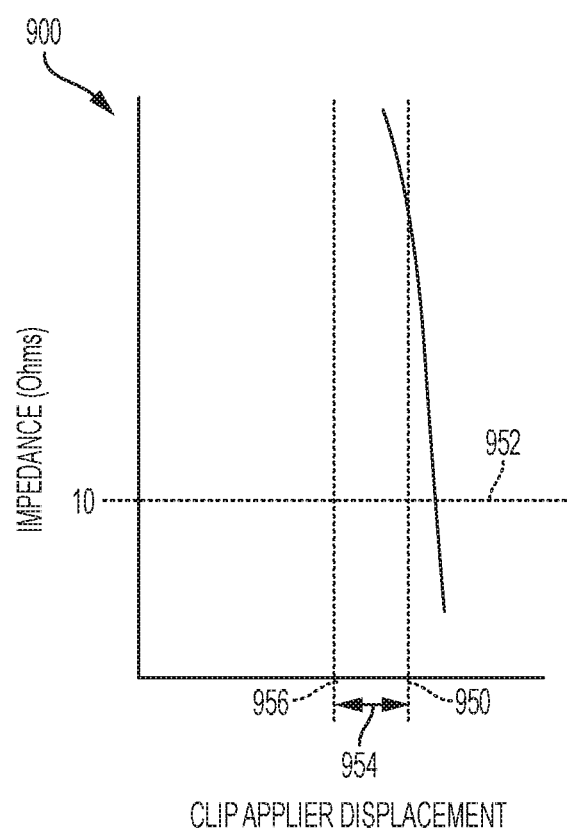
FIG. 12A is an impedance graph showing a measured impedance of a jaw assembly as a function of displacement of the jaw assembly relative to tissue.
Figure 12B:
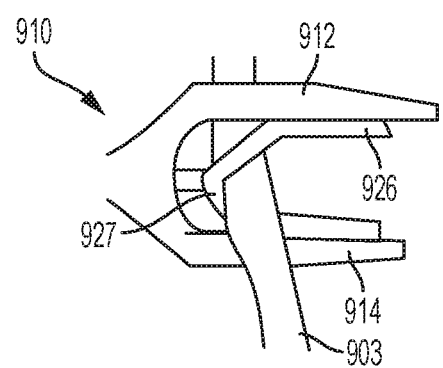
FIG. 12B is a top view of an embodiment of a jaw assembly showing tissue engaged within the jaws, with an apex of a clip positioned between the jaws of the jaw assembly.
Figure 12C:
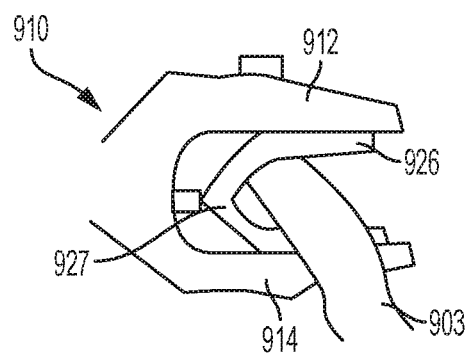
FIG. 12C is a top view of the jaw assembly of FIG. 12B showing the jaw assembly retracted to position the tissue in a desired location between the jaws for properly forming the clip to the tissue.

FIG. 12A illustrates an impedance graph 900 showing a measured impedance of a jaw assembly 910 of a surgical clip applier (e.g., as shown in FIGS. 12B and 12C), as indicated along the y-axis, relative to a displacement of the jaw assembly, as indicated along the x-axis. When the jaw assembly 910 is not in contact with anything, such as tissue, the measured impedance can be infinitely large. However, after the jaw assembly 910 is advanced and comes into contact with tissue, the impedance can be sharply reduced. For example, as shown in FIG. 12A, at a first clip applier displacement position 950, tissue 903 can be engaged with an apex 927 of a clip 926 positioned between the jaws 912, 914 of the jaw assembly 910, as shown in FIG. 12B. Such tissue 903 contact with the apex 927 of the clip 926 can cause the measured impenence to significantly drop. The control system 258 can include a predefined impedance threshold 952 (e.g., approximately 10 ohms) that can allow the control system 258 to determine that the tissue is engaged within the apex 927 of the clip 926 when the measured impedance reaches and/or drops below such predefined impedance threshold 952.

As shown in FIG. 12C, the control system 258 can be configured to stop advancement of the jaw assembly 910 and retract the jaw assembly 910 a predetermined distance 954 to thereby place the jaw assembly 910 at a second clip applier displacement position 956, as shown in FIG. 12A. At the second clip applier displacement position 956 the tissue is properly positioned between the jaws to ensure effective clip formation in and/or around the tissue when the jaws 912, 914 are forced closed. For example, proper positioning of tissue 903 between the jaws 912, 914 can include positioning the tissue 903 at an approximate mid-point position along a length of the jaws and/or between parts of the jaws 912, 914 that are positioned parallel to each other prior to clip formation, as shown in FIG. 12C. As such, the predetermined distance 954 can be defined based on a distance between the apex 927 of the clip 926 and the proper positioning between the jaws 912, 914. Once the jaw assembly 910 has been retracted the predetermined distance 954, the control system 258 can activate the clip forming assembly to cause the jaws 912, 914 to close and form the clip 926 in and/or around the properly positioned tissue 903. This can save procedure time and reduce procedure errors by ensuring proper clip formation in and/or around tissue.

Clip Stability Test

After activating a handheld clip applier to thereby close the jaws and form a clip positioned therebetween, some surgeons perform one or more steps to ensure the clip is properly secured within tissue before opening the jaws to allow release of the clip from the jaws. For example, prior to opening the jaws, the surgeon may cause the jaws to rotate and observe whether the clip appears to be properly engaged and secured within the tissue of a patient. If the clip appears to be properly engaged and secured, the surgeon may then allow the jaws to open and release the clip. However, if the clip does not appear to be properly engaged and secured, the surgeon can, for example, retract the jaws and clip positioned therebetween for releasing the clip from the jaws outside of the patient to prevent surgical errors and damage to the patient resulting from an unsecured and improperly positioned clip.

In some embodiments, the control system 258 is configured to perform a clip stability test to ensure a clip is properly formed and secured in tissue prior to releasing the clip. For example, after full jaw closure and clip formation, the control system 258 can activate the drive system (such as the drive system 150 shown in FIG. 3) to perform the clip stability test before fully opening the jaws to release the formed clip. As will be described in greater detail below, the clip stability test provides a measurable way for the control system to determine whether the clip is secured within the tissue. As such, not only does the clip stability test described herein provide a benefit of ensuring the clip is properly secured within tissue, but does so in a more reliable way than what is currently performed by surgeons who, instead, rely on visual ques.

Figure 13:
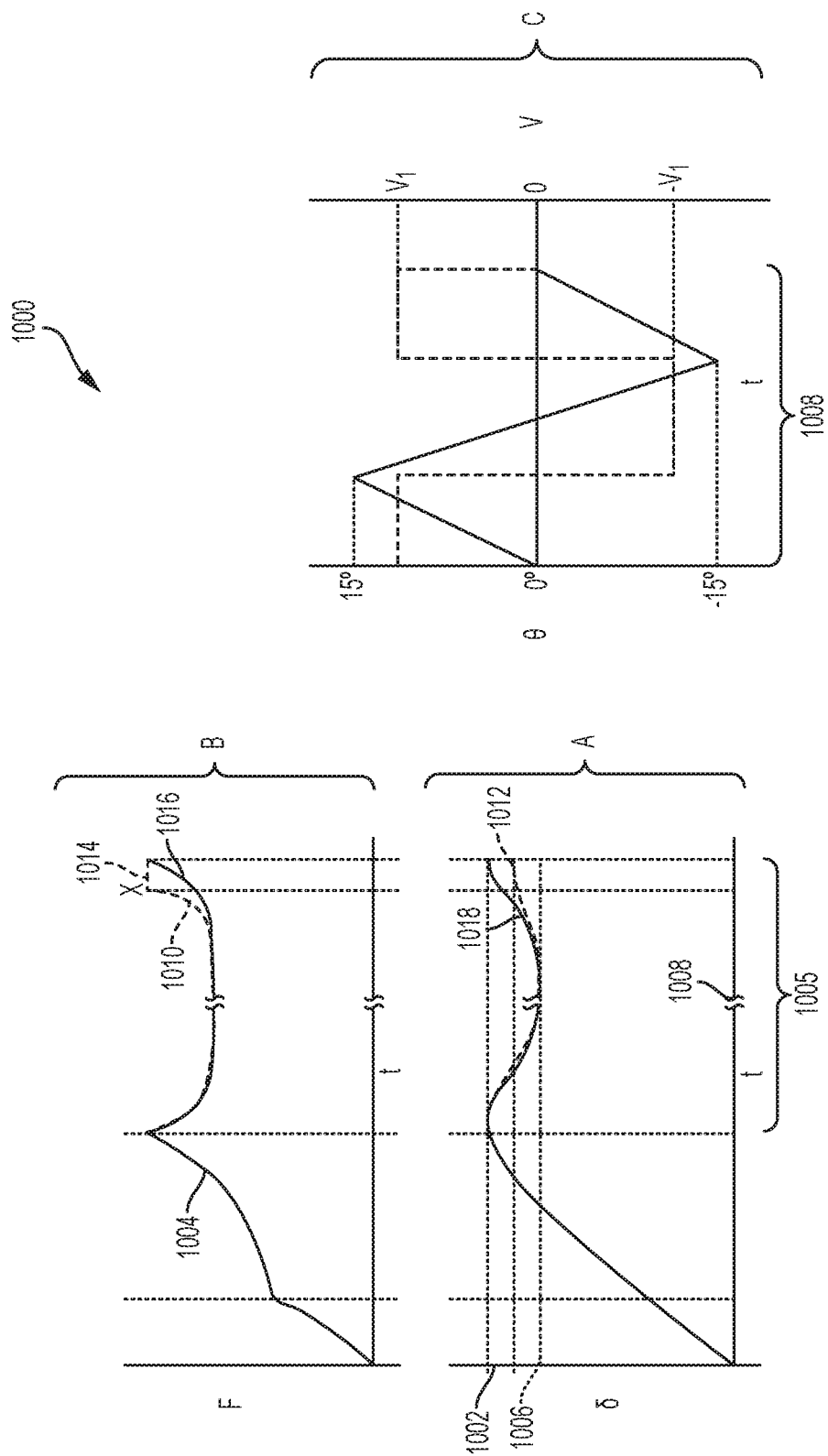
FIG. 13 is a graph showing monitored and controlled parameters for a clip stability test for determining clip engagement in tissue, including a displacement graph shown in section A, a related force graph shown in section B, and a related angles and velocities of rotation graph shown in section C.

FIG. 13 illustrates a clip stability test graph 1000 showing various parameters that are monitored and controlled by the control system during at least the performance of the clip stability test. As shown in FIG. 13, the clip stability test graph 1000 includes a section A having a y-axis that shows an example displacement of a cam (e.g., such as the cam 134 shown in FIG. 2) as a function time shown along the x-axis. As discussed above, distal displacement of the cam causes the jaws to fully close and form a clip therebetween, which is indicated in section A as a jaw closure displacement position 1002. Section B shows measured forces (e.g., indicated along the y-axis) associated with driving the cam. For example, as shown in sections A and B, a peak clip formation force 1004 occurs when the cam reaches the jaw closure displacement position 1002.

At the jaw closure displacement position 1002, the clip positioned between the jaws is intended to be fully formed and secured in tissue. As such, after the cam reaches the jaw closure displacement position 1002, the control system can activate the drive system to perform the clip stability test 1005, as shown in FIG. 13, to ensure that the clip is, in fact, properly secured in tissue before opening the jaws to release the clip.

As shown in section A, the clip stability test 1005 includes retracting the cam from the jaw closure displacement position 1002 to a partially open position 1006 where the jaws are caused to be in a partially open configuration. Such retracting of the cam can result in a drop in force applied to the cam, as shown in section B. When the cam is in the partially open position 1006, the jaws can be caused to rotate in at least one direction (e.g., during a jaw manipulation time range 1008), such as to rotate along a longitudinal axis of an elongate shaft having the jaws are positioned at a distal end thereof. Section C shows example angles and directions of rotation (e.g., indicated along the left y-axis) and example angular velocities associated with such rotations (e.g., indicated along the right y-axis) over time (e.g., indicated along the x-axis). For example, the time range in section C includes the jaw manipulation time range 1008 indicated with respect to section A. Such rotation or manipulation of the jaws when in the partially open configuration allows a clip that is secured in tissue to become misaligned with the jaws which can result in different displacement and force readings compared to a clip that is not properly secured in tissue and thus does not become misaligned with the jaws, as will be described in greater detail below.

As shown in section A, the clip stability test further includes distally advancing the cam after the jaws are caused to rotate in the partially open configuration. As the cam is distally advanced, the measured forces to advance the cam can increase, as shown in section B. If the clip is properly formed in tissue and thus becomes misaligned in the jaws during rotation of the jaws, as indicated by a first force line 1010 in section B and a first displacement line 1012 in section A, a force threshold 1014 will be reached before the cam is able to move back to the jaw closure displacement position 1002. As shown in section B, the force threshold 1014 can be equivalent to the peak clip formation force 1004. Such reaching of the force threshold 1014 before the cam is moved back to the jaw closure displacement position 1002 can be due, for example, to the clip being angled within the jaws and thus interfering with the jaws being able to fully close. However, if the clip is not properly formed in tissue and remains aligned in the jaws during rotation of the jaws, as indicated by a second force line 1016 in section B and a second displacement line 1018 in section A, the force threshold 1014 will not be reached until the cam is moved back to the jaw closure displacement position 1002. As such, the control system can monitor and measure such displacement and force measurements to determine whether the clip is properly formed in tissue before allowing the jaws to release the clip. For example, if the control system 258 determines that the clip is not properly secured in tissue, the control system can cause the robotic arm to remove the jaw assembly from the patient to release the formed clip from the jaws outside of the patient. However, if the control system 258 determines that the clip is properly secured in tissue, the control system can cause the jaws to fully open thereby releasing the formed clip to remain engaged in the tissue.

Computer Systems

As discussed above, the control systems disclosed herein can be implemented using one or more computer systems, which may also be referred to herein as digital data processing systems and programmable systems.

One or more aspects or features of the control systems described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computer system may include clients and servers. A client and server are generally remote from each other and typically interact through a communication network. The relationship of client and server arises by virtue of computer programs running on the respective computers and having a client-server relationship to each other.

The computer programs, which can also be referred to as programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, e.g., a mouse, a trackball, etc., by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

Figure 14:
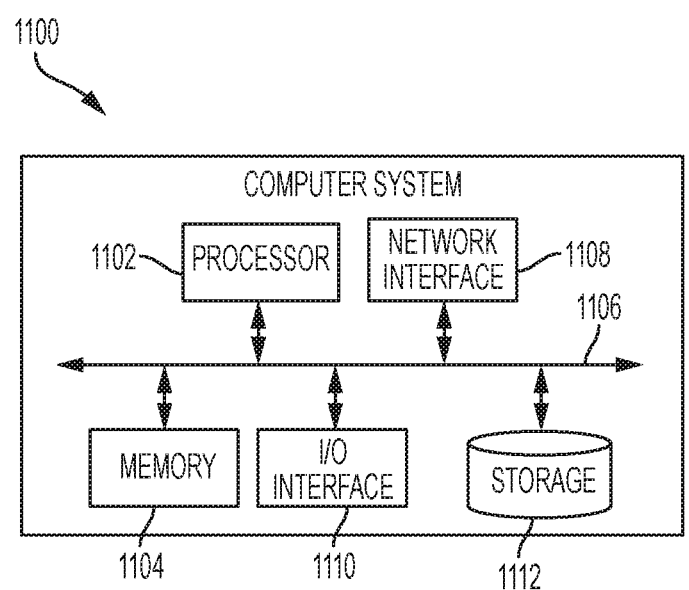
FIG. 14 is one exemplary embodiment of a computer system.

FIG. 14 illustrates one exemplary embodiment of a computer system 1100. As shown, the computer system 1100 includes one or more processors 1102 which can control the operation of the computer system 1100. "Processors" are also referred to herein as "controllers." The processor(s) 1102 can include any type of microprocessor or central processing unit (CPU), including programmable general-purpose or special-purpose microprocessors and/or any one of a variety of proprietary or commercially available single or multi-processor systems. The computer system 1100 can also include one or more memories 1104, which can provide temporary storage for code to be executed by the processor(s) 1102 or for data acquired from one or more users, storage devices, and/or databases. The memory 1104 can include read-only memory (ROM), flash memory, one or more varieties of random access memory (RAM) (e.g., static RAM (SRAM), dynamic RAM (DRAM), or synchronous DRAM (SDRAM)), and/or a combination of memory technologies.

The various elements of the computer system 1100 can be include a bus system 1106. The illustrated bus system 1106 can include an abstraction that represents any one or more separate physical busses, communication lines/interfaces, and/or multi-drop or point-to-point connections, connected by appropriate bridges, adapters, and/or controllers. The computer system 1100 can also include one or more network interface(s) 1108 that enable the computer system 1100 to communicate with remote devices, e.g., motor(s) coupled to the drive system that is located within the surgical device or a robotic surgical system, one or more input/output (TO) interface(s) 1110 that can include one or more interface components to connect the computer system 1100 with other electronic equipment, such as the sensors located on the motor(s), and one or more storage device(s) 1112. The storage device(s) 1112 can include any conventional medium for storing data in a non-volatile and/or non-transient manner. The storage device(s) 1112 can thus hold data and/or instructions in a persistent state, i.e., the value(s) are retained despite interruption of power to the computer system 1100.

A computer system can also include any of a variety of other software and/or hardware components, including by way of non-limiting example, operating systems and database management systems. Although an exemplary computer system is depicted and described herein, it will be appreciated that this is for sake of generality and convenience. In other embodiments, the computer system may differ in architecture and operation from that shown and described here.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical clip applier system, comprising:
a clip applier shaft assembly having a shaft with plurality of clips disposed therein and a pair of jaws at a distal end thereof, the clip applier shaft assembly including a clip advancing assembly configured to feed a distal-most clip of the plurality of clips into the pair of jaws, and a clamping assembly configured to move the pair of jaws from an open position to a closed position to form the distal-most clip around tissue;
a drive assembly operably coupled to the clamping assembly and configured to drive the clamping assembly through stages of clip formation in which the distal-most clip in the jaws is moved from an initial open configuration to a final closed configuration; and
a control system configured to actuate the drive assembly via a motor operatively coupled to the drive assembly and the control system, the control system having a stored predetermined threshold of torque applied to the drive assembly by the motor, the applied torque measured by a sensor operably coupled to the motor and the control system, and the control system being configured to stop movement of the drive assembly during the stages of clip formation if the applied torque measured by the sensor exceeds the stored predetermined threshold.

2. The surgical clip applier system of claim 1, wherein the control system is further configured to control a velocity of the clamping assembly if the applied torque measured by the sensor exceeds the stored predetermined threshold.

3. The surgical clip applier system of claim 1, wherein the drive assembly is disposed within a housing coupled to a proximal end of the clip applier shaft assembly.

4. The surgical clip applier system of claim 1, wherein the drive assembly comprises a first housing on a robotic arm having the motor disposed therein, and a second housing on a proximal end of the clip applier shaft assembly and having at least one connector for coupling to the motor in the first housing.

5. The surgical clip applier system of claim 1, wherein the stages of clip formation include a first stage in which the clip is moved from the initial open configuration to a partially closed configuration, and a second stage in which the clip is moved from the partially closed configuration to the final closed configuration, and wherein the stored predetermined threshold comprises a first threshold and a second threshold that differs from the first threshold, and wherein the control system is configured to stop movement of the drive assembly during the first stage of clip formation if the first threshold is exceeded, and the control system is further configured to stop movement of the drive assembly during the second stage of clip formation if the second threshold is exceeded.

6. The surgical clip applier system of claim 5, wherein the second threshold is greater than the first threshold.

7. A surgical clip applier system, comprising:
an electromechanical tool shaft assembly having
an instrument shaft,
an end effector at a distal end thereof having a pair of jaws movable between open and closed positions,
a clip stack disposed within the instrument shaft and comprising a plurality of clips,
a clip advancing assembly extending through the instrument shaft and configured to feed a distal-most clip of the clip stack into the pair of jaws,
a clamping assembly configured to move the pair of jaws from the open position to the closed position to move the distal-most clip in the pair of jaws from an open configuration to a tissue-engaging configuration;
a drive system operably coupled to the electromechanical tool shaft assembly and having at least one motor configured to apply an amount of torque to drive the clamping assembly through stages of clip formation including a first stage in which the pair of jaws are moved from the open position to a partially closed position to partially close the distal-most clip disposed within the pair of jaws, and a second stage in which the pair of jaws are moved from the partially closed position to the closed position to move the clip to the tissue-engaging configuration, the at least one motor operably coupled to a sensor configured to measure the amount of torque applied by the at least one motor; and
a control system operably connected to the at least one motor and the sensor, the control system configured to actuate the drive system and thereby control movement of the clamping assembly, the control system having a first threshold of torque applied to the drive system by the motor for the first stage of clip formation and a second threshold of torque applied to the drive system by the motor for the second stage of clip formation, the control system being further configured to terminate movement of the clamping assembly during the first stage if the applied torque measured by the sensor exceeds the first threshold, and the control system being configured to terminate movement of the clamping assembly during the second stage if the applied torque measured by the sensor exceeds the second threshold.

8. The surgical system of claim 7, wherein the second threshold is greater than the first threshold.

9. The surgical system of claim 7, wherein the first and second thresholds comprise motor load thresholds that limit a load on the at least one motor.

10. The surgical system of claim 7, wherein the drive system is disposed within a housing coupled to a proximal end of the instrument shaft.

11. The surgical system of claim 7, wherein the drive system comprises a first housing on a robotic arm having the at least one motor disposed therein, and a second housing on a proximal end of the instrument shaft and having at least one connector for coupling to the at least one motor in the first housing.

* * * * *